US008933297B2

(12) United States Patent
Weterings et al.

(10) Patent No.: US 8,933,297 B2
(45) Date of Patent: Jan. 13, 2015

(54) *NICOTIANA BENTHAMIANA* PLANTS DEFICIENT IN XYLOSYLTRANSFERASE ACTIVITY

(75) Inventors: Koen Weterings, Raleigh, NC (US); Gerben Van Eldik, Zwijnaarde (BE)

(73) Assignee: Icon Genetics GmbH (DE)

( * ) Notice: Subject to any disclaimer, the term of this patent is extended or adjusted under 35 U.S.C. 154(b) by 463 days.

(21) Appl. No.: 13/376,912

(22) PCT Filed: Jun. 10, 2010

(86) PCT No.: PCT/EP2010/003749
§ 371 (c)(1),
(2), (4) Date: Dec. 8, 2011

(87) PCT Pub. No.: WO2010/145846
PCT Pub. Date: Dec. 23, 2010

(65) Prior Publication Data
US 2012/0083014 A1    Apr. 5, 2012

Related U.S. Application Data

(60) Provisional application No. 61/187,409, filed on Jun. 16, 2009.

(30) Foreign Application Priority Data

Jun. 15, 2009    (EP) .................... 09007817

(51) Int. Cl.
| *A01H 5/00* | (2006.01) |
| *A01H 5/10* | (2006.01) |
| *C12N 15/01* | (2006.01) |
| *C12N 15/113* | (2010.01) |
| *C12N 15/63* | (2006.01) |
| *C12N 15/82* | (2006.01) |
| *C12P 21/00* | (2006.01) |
| *C12N 5/04* | (2006.01) |
| *C12N 5/10* | (2006.01) |
| *C12N 15/54* | (2006.01) |
| *C12N 9/10* | (2006.01) |

(52) U.S. Cl.
CPC .......... *C12N 9/1077* (2013.01); *C12N 15/8257* (2013.01); *C12N 15/8258* (2013.01)
USPC ........ 800/276; 800/284; 800/317.3; 800/278; 800/285; 536/23.2; 536/24.5; 435/468; 435/69.1; 435/414; 435/193; 435/419

(58) Field of Classification Search
None
See application file for complete search history.

(56) References Cited

U.S. PATENT DOCUMENTS

| 4,511,503 A | 4/1985 | Olson et al. |
| 4,515,893 A | 5/1985 | Kung et al. |
| 5,693,762 A | 12/1997 | Queen et al. |
| 5,721,108 A | 2/1998 | Robinson et al. |
| 5,725,856 A | 3/1998 | Hudziak et al. |
| 5,736,137 A | 4/1998 | Anderson et al. |
| 6,423,885 B1 | 7/2002 | Waterhouse et al. |
| 2005/0144667 A1 | 6/2005 | Stanley et al. |
| 2006/0253928 A1* | 11/2006 | Bakker et al. ............ 800/284 |

FOREIGN PATENT DOCUMENTS

| WO | 8903887 | 5/1989 |
| WO | 8908145 | 9/1989 |
| WO | 8910396 | 11/1989 |
| WO | 9213956 | 8/1992 |
| WO | 9303161 | 2/1993 |
| WO | 9606932 | 3/1996 |
| WO | 9612028 | 4/1996 |
| WO | 9630046 | 10/1996 |
| WO | 9640210 | 12/1996 |
| WO | 9640867 | 12/1996 |
| WO | 9713865 | 4/1997 |
| WO | 9845331 | 10/1998 |
| WO | 9953050 | 10/1999 |
| WO | 0112824 | 2/2001 |
| WO | 02088369 | 11/2002 |
| WO | 03076619 | 9/2003 |
| WO | 2004073390 | 9/2004 |
| WO | 2005047505 | 5/2005 |
| WO | 2005052170 | 6/2005 |
| WO | 2006012906 | 2/2006 |
| WO | 2006079546 | 8/2006 |
| WO | 2007107296 | 9/2007 |
| WO | 2008125972 | 10/2008 |
| WO | 2009056155 | 5/2009 |

OTHER PUBLICATIONS

R. Strasser et al., Generation of *Arabidopsis thaliana* plants with complex N-glycans lacking B1, 2-linked xylose and core al, 3-linked fucose, FEBS Letters, 2004, 132-136.
Bart M.G. Smit et al., Generation of gene knockouts and mutant models in the laboratory rat by ENU-driven target-selected mutagenesis, Pharmacogenetics and Genomics, vol. 16, 2006, p. 159-169.
Peter Rice et al., Emboss: The European Molecular Biology Open Software Suite, Resource Internet, TIG, Jun. 2000, vol. 16, No. 6, p. 276-277.
Johan Peleman et al., Structure and expression analyses of the S-adenosylmethionine synthetase gene family in *Arabidopsis thaliana*, Gene, vol. 84, 1989, 359-369.
S. Pagny et al., Structural requirements for *Arabidopsis* B1, 2-xylosyltransferase activity and targeting to the Golgi, The Plant Journal, 2003 33, 189-203.

(Continued)

Primary Examiner — David T Fox
Assistant Examiner — Stephen Uyeno
(74) Attorney, Agent, or Firm — Lerner, David, Littenberg, Krumholz & Mentlik, LLP

(57) ABSTRACT

The invention provides *Nicotiana benthamiana* mutant plants which are incapable of forming xylosyl-structures on glycoproteins. In addition, the invention provides methods for the production of heterologous glycoproteins in said mutant plants.

11 Claims, 6 Drawing Sheets

(56) References Cited

OTHER PUBLICATIONS

Figure 1A:
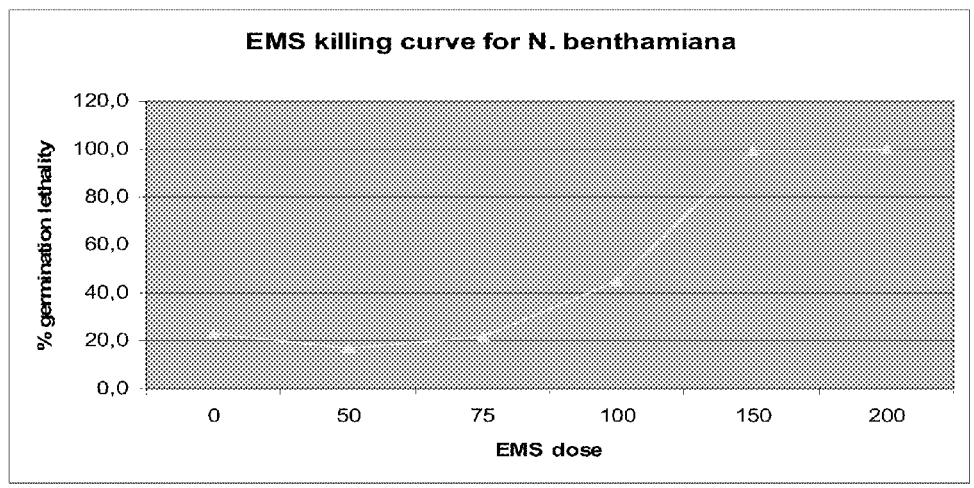

Claire M. McCallum et al., Targeted screening for induced mutations, Nature America Inc., Nature Biotechnology, Apr. 2000, vol. 18, p. 455-457.

Sylvestre Marillonnet et al., Systemic *Agrobacterium tumefaciens*-mediated transfection of viral replicons for efficient transient expression in plants, Nature Biotechnology, Jun. 2005, vol. 23, No. 6, p. 718-723.

Xin Li et al., A fast neutron deletion mutagenesis-based reverse genetics system for plants, The Plant Journal, 2001, 27(3), 235-242.

Daniel Kolarich et al., Comprehensive glyco-proteomic analysis of human α1-antitrypsin and its charge isoforms, Proteomics 2006, 6, 3369-3380.

B Keller et al., Specific expression of a novel cell wall hydroxyproline-rich glycoprotein gene in lateral root initiation, Genes Dev. 1989, 1639-1646.

Beat Keller et al., Glycine-rich cell wall proteins in bean: gene structure and association of the protein with the vascular system, The EMBO Journal, 1988, vol. 7, No. 12 pp. 3625-3633.

Michael Keil et al., Both wound-inducible and tuber-specific expression are mediated by the promoter of a single member of the potato inhibitor II gene family, The EMBO Journal, 1989, vol. 8, No. 5 pp. 1323-1330.

Chunsheng Jin et al., Immunoglobulin G specifically binding plant N-glycans with high affinity could be generated in rabbits but not in mice, Glycobiology vol. 16, No. 4 pp. 349-357, 2006.

Richard L. Hudspeth et al., Structure and expression of the maize gene encoding the phosphoenolpyruvate carboxylase isozyme involved in C4 photosynthesis, Plant Molecular Biology 12: 579-589, 1989.

Mark H. Harpster et al., Relative strengths of the 35S califlower mosaic virus, 1, 2, and nopaline synthase promoters in transformed tobacco sugarbeet and oilseed rape callus tissue, Mol Gen Genet, 1988 212: 182-190.

L. Faye et al., Affinity Purification of Antibodies Specific for Asn-Linked Glycans Containing x1-3 Fucose or B1-2 Xylose, Analytical Biochemistry 209, 104-108, 1993.

Jenny Bostrom et al., Variants of the Antibody Herceptin that Interact with HER2 and VEGF at the Antigen Binding Site, Science, Mar. 20, 2009, vol. 323, p. 1610-1614.

Yong-Qiang an et al., Conserved Expression of the *Arabidopsis* ACT1 and ACT3 Actin Subclass in Organ Primordia and Mature Pollen, The Plant Cell, vol. 8, Jan. 15-30, 1996.

Stefan Weckx et al., novoSNP, a novel computational tool for sequence variation discovery, Genome Res. 2005 15: 436-442.

Klein, S.L., et al., Genetic and Genomic Tools for *Xenopus* Research: The NIH *Xenopus* Initiative, Dev. Dyn. vol. 225 No. 4, 384-391, 2002, NP_001016664.

Magdaleno, S., et al., A High-Resolution Anatomical Atlas of the Transcriptome in the Mouse Embryo, PLoS Biol. vol. 9 No. 1, E1000582, 2011, NM_146045.

Diez-Rouz, G., et al., A high-resolution anatomical atlas of the transcriptome in the mouse embryo, PLoS Biol. vol. 9, No. 1, E1000582, 2011, NM_022305.

Wei, Y. et al., Betal, 4-galactosyltransferase V regulates self renewal of glioma-initiating cell, Biochem. Biophys. Res. Commun., 396 (3), p. 602-607, 2010, NM_004776.

Wang, Y. et al., Betal, 4-Galactosyltransferase-I contributes to the inflammatory processes in synovial tissue of patients with rheumatoid arthritis, Inflamm. Res., 59 (12), p. 1009-1018, 2010, NM_001497.

Cox, K.M., et al., Direct Submission, Submitted (Jun. 21, 2006) Molecular Biology, Biolex, Inc. 158 Credle Street, Pittsboro, NC 27312, USA, DQ789145.

Castilho, A., et al., Genomic characterization and physical mapping of two fucosyltransferase genes in *Medicago truncatula*, Genome vol. 48, No. 1, 168-176, 2005, AY557602.

Sourrouille, C., et al., Direct Submission, Submitted Mar. 6, 2002, LTI-CNRS UMR6037, Universite de Rouen, Bat. Extension Biologie, Mont Saint Aignan 768, France, AY082445.

Sasaki, T., et al., *Oryza sativa* nipponbare (GA3) genomic DNA, chromosome 8, PAC clone: P0013B04, Published only in Database, 2001, AP004457.

Horstmann, V. et al., Quantitative promoter analysis in *Physcomitrella patens*: a set of plant vectors activating gene expression within three orders of magnitude, BMC Biotechnol vol. 4, No. 13, 2004, AJ618932.

Sourrouille, C., et al., Direct Submission, Submitted Mar. 6, 2002, LTI-CNRS UMR60374, Universite de Rouen, Bat. Extension Biologie, Mont Saint Aignan 76821, France, AAL99371.

Leiter, H. et al., Purification, cDNA cloning, and expression of GDP-L-FUC:Asn-linked GlcNAc Alpha1,3-fucosyltransferase from mung beans, J. Biol. Chem. vol. 274, No. 31, 21830-21839, 1999, Y18529.

* cited by examiner

XylTg14

Figure 2

XylTg19

```
                                                                                              XylTg19-2
   1    CACCTTGTTT CTGTCTTCGC TCTCAACTCA ATCACTCTCT ATCTCTACTT CTCTTCCCAC CCTGATCACA AATCCCCCCA AAACCACTTT TCCTTGTCGG
        GTGGAACAAA GAGAGAAGCG AGAGTTGAGT TAGTGAGAGA TAGAGATGAA GAGAAGGGTG GGACTAGTGT TTAGGGGGGT TTTGGTGAAA AGGAACAGCC
                                                    XylTg19-1                                 XylTg19-2
                                                        T                                         A
 101    AAAACCACCA TCATAATTTC CACTCTTCAA TCACTTCTCA ATATTCCAAG CCTTGGCCTA TTTTGCCCTC CTACCTCCCT TGGTCTCAAA ACCCTAATGT
        TTTTGGTGGT AGTATTAAAG GTGAGAAGTT AGTGAAGAGT TATAAGGTTC GGAACCGGAT AAAACGGGAG GATGGAGGGA ACCAGAGTTT TGGGATTACA
 201    TGCTTGGAGA TCGTGCGAGG GTTACTTCGG TAATGGGTTT ACTCTCAAAG TTGACTTTCT CAAAACTTCG CGGGAGTTTC ACCGGAAATT CGGGGATAAC
        ACGAACCTCT AGCACGCTCC CAATGAAGCC ATTACCCAAA TGAGAGTTTC AACTGGAAGA GTTTTGAAGC GGCCTCAAAG TGGCCTTTAA GCCGCTATTG
                                                                                                              NBNPGS2
                                                                                                                  T
 301    ACCGTCTCCG GTGACGGCGG ATGGTTTAGG TGTTTTTTCA GTGAGACTTT GCAGAGTTCG ATCTGCGAGG GAGGCGCAAT ACGAATGAAT CCGGACGATA
        TGGCCAGAGGC CACTGCCGCC TACCAAATCC ACAAAAAGT CACTCTGAAA CGTCTCAAGC TAGAGCGCTCC CTCGGCGTTA TGCTTACTTA GGCCTGCTAT
 401    TTTTGATGTC TCGTGGAGGT GAGAAATTGG AGTCGGTTAT TGGTAGGAAT GAAGATGATG AGCTGCCCAT GTTCAAAAAT GGAGCTTTCC AAATTGAAGT
        AAAACTACAG AGCACCTCCA CTCTTTAACC TCAGCCAATA ACCATCCTTA CTTCTACTAC TCGACGGGTA CAAGTTTTTA CCTCGAAAGG TTTAACTTCA
                                                                                           NBNPGS2
                                                                                               A
 501    TACTGATAAA CTGAAAATTG GGAAAAAACT AGTGGATAAA AAATTCTTGA ATAAATACTT ACCGGGAGGT GCGATTTCAA GGCACACTAT GCGTGAGTTA
        ATGACTATTT GACTTTTAAC CCTTTTTTGA TCACCTATTT TTTAAGAACT TATTTATGAA TGGCCCTCCA CGCTAAAGTT CCGTGTGATA CGCACTCAAT
                                                        NBNPGS2
                                                           T
 601    ATTGACTCTA TTCAGTTGGT TGGCGCCGAT GAATTTCACT GTTCTGAGGT TAGATTTTGA TATTTATTTG ATCTTTAAAT TAGAGGTTTG AACTTTGTTA
        TAACTGAGAT AAGTCAACCA ACCGGGCTA CTTAAAGTGA CAAGACTCCA ATCTAAAACT ATAAATAAAC TAGAAATTTA ATCTCCAAAC TTGAAACAAT
 701    ATGTTGGCAG ATATGGAATA CAATAATGGA TTTTGTTTGA TCTGTTTAAT GAAGATTGTC TAAAACCTCA ATGCTATAAA TATTTGTTTG TTTGCTTCAT
        TACAACCGTC TATACCTTAT GTTATTACCT AAAACAAACT AGACAAATTA CTTCTAACAG ATTTTGGAGT TACGATATTT ATAAACAAAC AAACGAAGTA
 801    TAATTAAAGA GAATATCCCG ACTAGATGCC AGATAACACC AGTTAGTTGA CTTTTGGATT GGGTTGCATT TCATTTAATC AGATATGGTA CTCATTCTTA
        ATTAATTTCT CTTATAGGGC TGATCTACGG TCTATTGTGG TCAATCAACT GAAAACCTAA CCCAACGTAA AGTAAATTAG TCTATACCAT GAGTAAGAAT
 901    AATGTTTCAC TAAAGAATTT GTCAAGATTT CAGAGTTTAT ATATAGGTGT ATTTGGAATT CTGGATTTGG ATCTAGTATT GAATGGATTA CTGAATTTGT
        TTACAAAGTG ATTTCTTAAA CAGTTCTAAA GTCTCAAATA TATATCCACA TAAACCTTAA GACCTAAACC TAGATCATAA CTTACCTAAT GACTTAAACA
1001    ACTCCCCAGT CATCAGGGGA GGAGCAATAG ATCGAATTCA AGGGTTGAAA AGTAATACTG AGTCAGAAAT TAACCACTTT AACTTGGAAA CGGTAAATGT
        TGAGGGGTCA GTAGTCCCCT CCTCGTTATC TAGCTTAAGT TCCCAACTTT TCATTATGAC TCAGTCTTTA ATTGGTGAAA TTGAACCTTT GCCATTTACA
1101    ATGTGTTCTA AGATGATTAT TCCTATAACT TTTGATGTCT AATATGGAGA AAGTGAGTTG ATTTATGCTT TTTCCTTTTC CCTTTATTGA TGTTGGTTTT
        TACACAAGAT TCTACTAATA AGGATATTGA AAACTACAGA TTATACCTCT TTCACTCAAC TAAATACGAA AAAGGAAAAG GGAAATAACT ACAACCAAAA
1201    TAAATTCTAT CAATTCCCTT GTTTGGTTGC TACTCAAATT GAACCTTAGA CGGAGTAGCA ATAGCAAAAA GTGAAGAAAG GACATTTTTT TCTCCTTTCA
        ATTTAAGATA GTTAAGGAAA CAAACCAACG ATGAGTTTAA CTTGGAATCT GCCTCATCGT TATCGTTTTT CACTTCTTTC CTGTAAAAAA AGAGGAAAGT
1301    TCTCTTTATT TCCGTTTGAC ATACAGAATA CGGTAGCATC TGCCTGAAGT GGTTAATTTC ATTCCTTAAA ATTTGCATAA CTAATATTTC CGTTTTTGTT
        AGAGAAATAA AGGCAAACTG TATGTCTTAT GCCATCGTAG ACGGACTTCA CCAATTAAAG TAAGGAATTT TAAACGTATT GATTATAAAG GCAAAAACAA
1401    TTTGTTTATC TTTTCCATTG GCATGCCATG TTATTTTTGG TTTAGGTTTA CATAATTATT TATGTGATTT CGATGGAGT TACTAATGAT TTTTTGTTTT
        AAACAAATAG AAAAGGTAAC CGTACGGTAC AATAAAAACC AAATCCAAAT GTATTAATAA ATACACTAAA GACTACCTCA ATGATTACTA AAAAACAAAA
1501    TGTTTTTGTT TTTTTCTTTT CCTTTTCTCT AGTCGAGGGT CGATTGGAAA TAGCCTCTCT GCCCTTTTGA ATAGGGGTAA GGCTCGGGTA CGTGTACCAT
        ACAAAAACAA AAAAAGAAAA GGAAAAGGAC TCAGCTCCCA GCTAACCTTT ATCGGAGACA CGGGAAAACC TATCCCCATT CCGGACCCAT GCACATGGTA
1601    CCCCAGACCC CACTCTGTGG GACTATACCG GGTAGTTGTT GTGTTGTAAA TTCGAGTAAA TGCCTTTTGA ACCTTTAGTT GAATAGTTGT ACAACTGGTT
        GGGGTCTGGG GTGAGACACC CTGATATGGC CCATCAACAA CAACAACATT AAGCTCATTT ACGGAAAACT TGGAAATCAA CTTATCAACA TGTTGACCAA
1701    GTTGCATTTT GAGGACTATC GACTTGATTT GACACTTTAC ATGAAAACTT TTATCTAGGA AGAAATCCCT ACCAGAGATA GGGAGCTGTC GCTTGGTTAT
        CAACGTAAAA CTCCTGATAG CTGAACTAAA CTGTGAAATG TACTTTTGAA AATAGATCCT TCTTTAGGGA TGGTCTCTAT CCCTCGACAG CGAACCAATA
1801    GAGCTACTGG CTTAAAGTTT GAGTTTGACC TATTAATTTT AGATCTTCAC CAGGATAACA TCTAGAGTTT AATTAAATTC TCAAGCAGTA TTTTGCACTA
        CTCGATGACC GAATTTCAAA CTCAAACTGG ATAATTAAAA TCTAGAAGTG GTCCTATTGT AGATCTCAAA TTAATTTAAG AGTTCGTCAT AAAACGTGAT
1901    ATAAGGGGAA CACATGAAGG ATGTAGCACT ACTACGTTAT GTTCTTTATT TACTATTGAT TGACAACCAG CTTAAATGAT GACAAATGGT CTTATATTTG
        TATTCCCCTT GTGTACTTCC TACATCGTGA TGATGCAATA CAAGAAATAA ATGATAACTA ACTGTTGGTC GAATTTACTA CTGTTTACCA GAATATAAAC
2001    CTTTTTTACA TTGCTCATGA CTTGGGATAT TTTTGAATCA ACATTTTTCG GTTCTTTATG TACTTATCAA AAAATTATCC CTGCTAGATG TTAGTGTTCA
        GAAAAAATGT AACGAGTACT GAACCCTATA AAAACTTAGT TGTAAAAAGC ATGAATAGTT TTTTAATAGG GACGATCTAC AATCACAAGT
2101    AGCAACATGC TAGCTTTTAA GGAAGCTCCT TCTTTGATTC ATGCCATCTT TCCGAAGCCT TACGTTTCTG TCATTTTTCT AATTTTCATT TCAGTGGGTT
        TCGTTGTACG ATCGAAAATT CCTTCGAGGA AGAAACTAAG TACGGTAGAA AGGCTTCGGA ATGCAAAGAC AGTAAAAGAC AGTAAAAGTAA AGTCACCCAA
2201    GAGGAGCCGT CACTTTTGAT TACACGATTT GAGTATGCAA ACCTTTTCCA CACAGTTACC GATTGGTATA GTGCATACGC GGCATCCAGG GTTACTGGTT
        CTCCTCGGCA GTGAAAACTA ATGTGCTAAA CTCATACGTT TGGAAAAGGT GTGTCAATGG CTAACCATAT CACGTATGCG CCGTAGGTCC CAATGACCAA
2301    TGCCCAGTCG GCCAAATTTG GTTTTTGTAG ATGGCCATTG TGAGGTATGT TTGACAGTAT TGATAACGAT GGCATGCATT GTACTGTGTT ATGGATGAAA
        ACGGGTCAGC CGGTTTAAAC CAAAAACATC TACCGGTAAC ACTCCATACA AACTGTCATA ACTATTGCTA CCGTACGTAA CATGACACAA TACCTACTTT
2401    GAAATGAAAC CATCAATTAT TTTCTAGTAG GCAATGCTCT TAAGATGCTT GTGTCAAATT GGTTAGAGTT AATCCTAAGT TTCTCTGAAT TTCCATTTGT TTGAGCTTTC
        CTTTACTTTG GTAGTTAATA AAAGATCATC CGTTACGAGA ATTCTACGAA CACAGTTTAA CCAATCTCAA TTAGGATTCA AAGGTAAACA AACTCGAAAG
2501    TGTTTGACTG ACTACAATAC TTGTCCCAAT ACCTAGTTGT TGCGGTTGGC TCATTCTTAC TTCTATTTAC GTGTCACTGT TTCTCTGAAT GGTCCCTTTG
        ACAAACTGAC TGATGTTATG AACAGGGTTA TGGATCAACA ACGCCAACCG AGTAAGAATG AAGTAAATATG CACAGTGACA AAGAGACTTA CCAGGGAAAC
2601    TGGTGAAAAG AGCTTTTGCT ATGTAGAAAA ACTAGGAAGA ATTTCATTTC TGGAGCAACT TATTTTTACC TATTACACCG TCTCATAAAA TTGCTTCTAA
        ACCACTTTTC TCGAAACGA TACATCTTTT TGATCGTTTC TAAAGTAAAG ACCTCGTTGA ATAAAAAATGG AATGTAGTGC AGAGTATTTT AACGAAGATT
2701    CTGTATACTT TAATTCTTGG AGAGATGCTT TCATGTGAAT AAAGTTCTTT CACTCCACTA CTGGAAGCTT GCTGCATGAA ATTTACTTGG CCATACTGGG
        GACATATGAA ATTAAGAACC TCTCTACGAA AGTACACTTA TTTCAAGAAA GTGAGGTGAT GACCTTCGAA CGACGTACTT TAAATGAACC GGTATGACCC
2801    GCCGTGTTTT GATTTGTCTT CAAATTCATT TTCTTCATGT AGTTCTTTCG AGTAATATTT TTCCTCCTCA GGTCCGAAGC TTAGTTCCTA TGTTTGAAAA AAATTCAGAC ACAATTGGAG
        CGGCACAAAA CTAAACAGAA GTTAAGTAA AAGAAGTACA TCAAGAAAGC TCATTATAAA AAAGGAGAAG ACAAACTTTT TTAAGTCTG TGTTAACCTC
2901    GAAACATGGA AAGCACTTTT TTCAAGCCTC ACTTATGCTA AGAACTTTAG TGGCCCAGTT TGTTTCCGTC ATGCTGTCCT CTCGCCTTTA GGATATGAAA
        CTTTGTACCT TTCGTGAAAA AAGTTCGGAG TGAATACGAT TCTTGAAATC ACCGGGTCAA ACAAAGGCAG TACGACAGGA GAGCGGAAAT TTTAACTCTT
3001    CTGCCCTGTT TAAGGGACTG TCAGAAACTA TAGATTGTAA TGGAGCTTCT GCTCATGATT TGTGGCAAAA GCCTGATGAT AAAAAAACTG CACGGTTGTC
        GACGGGACAA ATTCCCTGAC AGTCTTTGAT ATCTAACATT ACCTCGAAGA CGAGTACTAA ACACCGTTTT CGGACTACTA TTTTTTTGAC GTGCCAACAG
3101    CGAGTTTGGG GAGATGATCA GGGCAGCCTT TGGATTTCCT GTGGATAGAC AGAACATCCC AAGGACAGTC ACAGGCCCTA ATGTCCTCTT TGTTAGACGT
        GCTCAAACCC CTCTACTAGT CCCGTCGGAA ACCTAAAGGA CACCTATCTG TCTTGTAGGG TTCCTGTCAG TGTCCGGGAT TACAGGAGAA ACAATCTGCA
3201    GAGGATTATT TAGCTCACCC ACGTCATGGT GGAAAGGTAC AGTCTAGGCT TAGCAATGAA GAGCTAGTAT TTGATTCCAT AAAGAGCTGG GCCTTGAACC
        CTCCTAATAA ATCGAGTGGG TGCAGTACCA CCTTTCCATG TCAGATCCGA ATCGTTACTT CTCGATCATA AACTAAGGTA TTTCTGACAA CGGAACTTGG
3301    ACTCGGAGTG TAAATTAAAT GTAATTAACGA GATTGTTTGC CCACATGTCC ATGAAAGAGC AAGTTCCAGC AATCCAAGAT GCTTCTGTCA TTGTTGGTGC
        TGAGCCTCAC ATTAATTTA CATTAATTGC CTAACAAACG GGTGTACAGG TACTTTCTCG TTCAAGCTCG TTAAGTTCTA CGAAGACAGT AACAACCACG
3401    TCATGGAGCA GGTCTAACTC ACATAGTTTC TGCAGCACCA AAAGCTGTAA TACTAGAAAT TATAAGCAGC GAATATAGGC GCCCCCATTT TGCTCTGATT
        AGTACCTCGT CCAGATTGAC GTATCAAAG ACGTGCTGGT TTCGACATT ATGATCTTTA ATATTCGTCG CTTATATCCG CGGGGGTAAA ACGAGACTAA
3501    GCACAATGGA AAGGATTGAA GTACCATCCA ATATATTTGG AGGGGTCTTA TGCGGATCCT CCAGTTGTGA TCGA
        CGTGTTACCT TTCCTAACCT CATGGTAGGG TATATAAACC TCCCCAGAAT ACGCCTAGGA GGTCAACAGT AGCT     (SEQ ID NO:3)
```

Figure 2 Continued

NICOTIANA BENTHAMIANA PLANTS DEFICIENT IN XYLOSYLTRANSFERASE ACTIVITY

CROSS-REFERENCE TO RELATED APPLICATIONS

This application is a §371 U.S. National Stage of International Application No. PCT/EP2010/003749, filed Jun. 10, 2010, which claims the benefit of European Patent Application Serial No. 09007817.1, filed Jun. 15, 2009, U.S. Patent Application Ser. No. 61/187,409, filed Jun. 16, 2009, the contents of which are herein incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named "9068PCTUSSeqListing.txt", created on Dec. 7, 2011, and having a size of 29,000 bytes and is filed concurrently with the specification. The sequence listing contained in this ASCII formatted document is part of the specification and is herein incorporated by reference in its entirety.

FIELD OF THE INVENTION

The current invention relates to the field of molecular farming, i.e. the use of plants and plant cells as bioreactors to produce biopharmaceuticals, particularly proteins with pharmaceutical interest such as therapeutic proteins, which have an N-glycosylation pattern that resembles mammalian glycosylation. The invention relates to plants of the genus *Nicotiana* which are deficient in xylosyltransferase activity, which plants may be applied as host plants or host cells to produce heterologous glycoproteins.

BACKGROUND

Glycosylation is the covalent linkage of an oligosaccharide chain to a protein resulting in a glycoprotein. In many glycoproteins, the oligosaccharide chain is attached to the amide nitrogen of an asparagine (Asn) residue and leads to N-glycosylation. Glycosylation represents the most widespread post-translational modification found in natural and biopharmaceutical proteins. It is estimated that more than half of the human proteins are glycosylated and their function frequently depends on particular glycoforms (glycans), which can affect their plasma half life, tissue targeting or even their biological activity. Similarly, more than one-third of approved biopharmaceuticals are glycoproteins and both their function and efficiency are affected by the presence and composition of their N-glycans. Leafy crops, such as the tobacco plant *Nicotiana benthamiana*, are an attractive system for the production of therapeutic proteins, as plants are generally considered to have several advantages, including the lack of animal pathogens such as prions and viruses, low cost and the large-scale production of safe and biologically active valuable recombinant proteins, the case of scale-up, efficient harvesting and storage possibilities. However, N-linked glycans from plants differ from those of mammalian cells. For example in plants, beta-(1,2)-xylose residues have been shown to be linked to the core Man3GlucNAc2-Asn of glycans, whereas they are not detected on mammalian glycans, where sialic acid residues and terminal beta(1,4)-galactosyl structures occur instead. The unique N-glycans added by plants could impact on both immunogenicity and functional activity of the protein and, consequently, may represent a limitation for plants to be used as a protein production platform. Indeed, the immunogenicity of beta-1,2-xylose residues in mammals has been described in for example Jin et al. (2006) Glycobiology 16: 349-357.

The enzyme that catalyses the transfer of xylose from UDP-xylose to the core β-linked mannose of protein-bound N-glycans is beta-1,2-xylosyltransferase ("XylT", EC 2.4.2.38). The beta-1,2-xyosytransferase is an enzyme unique to plants and some non-vertebrate animal species and does not occur in human beings or in other vertebrates.

WO2007107296 describes the identification and cloning of beta-1,2 xylosyltransferases from the genus *Nicotiana* such as *Nicotiana benthamiana*. Various strategies have been applied to avoid beta-1,2-xyosyl structures on glycoproteins produced by plants. WO2009056155 describes an RNA interference strategy for the generation of *Nicotiana benthamiana* plants which are deficient in the formation of beta-1,2-xyosyl structures as well as devoid of alfa-1,3-fucosyl structures on heterologous glycoproteins.

The cleanest approach for the production of glycoproteins lacking xylosyl-epitopes in *Nicotiana benthamiana* would be the generation of a full knock-out of the beta-1,2-xylosyl-transferase gene in this plant. The latter is however not a straight-forward strategy because of the documented presence of at least two beta-1,2-xylosyltransferases (see WO2007107296) and the extremely low efficiency of homologous recombination in plants. Another strategy would be the generation of null mutations in all of the functional alleles of the genes possessing beta-1,2 xylosyltransferase activity in *Nicotiana benthamiana*. Plant populations mutagenized by ethyl methanesulfonate (EMS) have proved invaluable to plant biologists as a means of dissecting genomic traits. *Nicotiana benthamiana* is however a higher plant and is estimated to contain 30.000 to 50.000. A major obstacle in *Nicotiana benthamiana* genetics is the lack of large mutant populations required for mutant gene identification. Such a useful *N. benthamiana* population would ideally contain at least one mutant allele for every *N. benthamiana* gene. Mutant *N. benthamiana* plants can be produced through the use of DNA damaging agents such as EMS, X-rays, or fast-neutrons. However, no stocks of mutagenized M2 seeds, originating from a large population of M1 plants, are available for screening mutations in candidate genes. The aim of our research was to provide a mutant population of *N. benthamiana*, to screen for null alleles in said population for genes that encode beta-1,2-xylosyltransferase activity with the ultimate goal to evaluate the possibility of obtaining an induced mutant plant completely deficient in the xylosyl-transferase activity.

SUMMARY OF THE INVENTION

In work leading up to the present invention, the inventors sought to inactivate by classical mutagenesis the beta-1,2-xylosyltransferase pathway in *Nicotiana benthamiana* which is involved in undesired N-glycosylation hampering the usefulness for the production of heterologous proteins in higher plants. In particular, the inventors have chemically mutagenized a wild type *Nicotiana benthamiana* plant and have identified null alleles of two beta-1,2-xylosyltransferase genes by classical mutagenesis in *Nicotiana benthamiana*. After combining said null alleles in a single plant, it was observed that homozygous double mutant *Nicotiana benthamiana* plant—comprising a homozygous combination of the four null alleles—proved to be viable and revealed no obvious, morphological phenotype under standard growth conditions. Most importantly, the resulting homozygous double mutant *N. benthamiana* plant was devoid of the complete xylosyltransferase pathway because it produced endogenous and heterologous glycoproteins which lacked beta-1,2-xylosyl sugar structures on said glycoproteins. Thus, the homozygous combination of the four null alleles proved to be sufficient for the elimination of the complete beta-1,2-xylosyltransferase activity in *Nicotiana benthamiana*.

It is therefore one object of the invention to provide a beta-1,2-xylosyltransferase null mutant of the plant *Nicotiana benthamiana*, or cells, parts, seed or progeny thereof, reference seed having been deposited on May 21, 2009 at the NCIMB under accession number NCIMB 41622. It is another object to provide a *Nicotiana benthamiana* plant or plant cell which is a beta-1,2-xylosyltransferase null mutant characterized by comprising a combination of homozygous null alleles selected from a null allele from the group consisting of xyltg14-1, xyltg14-2 or xyltg14-3 and a null allele, selected from the group consisting of xyltg19-1 or xyltg19-2. It is a further object to provide a plant or plant cell which does not form detectable levels of beta-1,2-xylosyl-sugars on N-glycan structures of glycoproteins produced in said plant.

It is another object to provide a *Nicotiana benthamiana* seed characterized as being homozygous for two null alleles, xyltg14-1 and xyltg19-1, of beta-1,2-xylosyltransferase, having been deposited at the NCIMB on May 21, 2009, under accession number NCIMB 41622.

In a further object a *Nicotiana benthamiana* plant, or a cell, part, seed or progeny thereof, obtained from the reference seed having been deposited at the NCIMB on May 21, 2009, under accession number NCIMB 41622.

In yet a further object the beta-1,2-xylosyltransferase null mutant of the plant or plant cell of *Nicotiana benthamiana* further comprises a silenced alpha-1,3-fucosyltransferase activity.

In yet another further embodiment the beta-1,2-xylosyltransferase null mutant of the plant or plant cell of *Nicotiana benthamiana* that comprises a silenced alpha-1,3-fucosyltransferase activity in addition also comprises a beta-1,4-galactosyltransferase activity.

In yet another further embodiment the beta-1,2-xylosyltransferase null mutant of the plant or plant cell of *Nicotiana benthamiana* that comprises a silenced alpha-1,3-fucosyltransferase activity and a beta-1,4-galactosyltransferase activity further comprises a chimeric gene encoding a heterologous protein.

In yet a further aspect the *Nicotiana benthamiana* plants described herein before are used for the production of heterologous proteins.

In yet a further aspect a method is provided to produce at least one heterologous protein in plants or plant cells according to any of claims 1-3 and 5-8 comprising the steps of a) providing a plant or plant cell according to any of claims 1-3 and 5-8 with at least one chimeric gene comprising the following operably linked nucleic acid molecules: i) a plant-expressible promoter, ii) a DNA region encoding a heterologous protein, and iii) a DNA region involved in transcription termination and polyadenylation, and b) cultivating said plant or plant cell and isolating said at least one heterologous protein from said plant or plant cell. In a particular aspect said heterologous protein is an antibody.

FIGURES

Figure 1B:
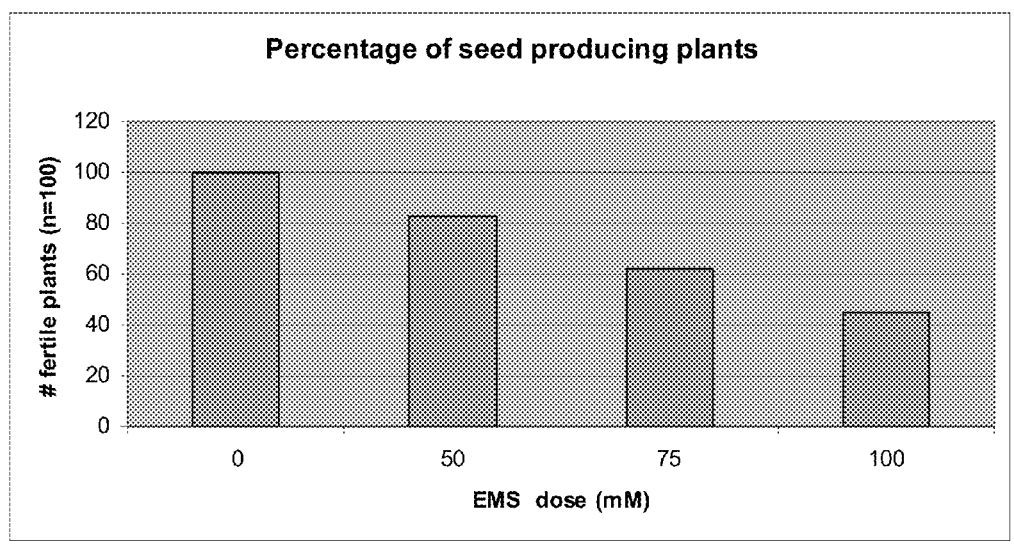

FIG. 1: FIG. 1A. Determination of the optimum EMS dose for production of M2 seeds in *N. benthamiana*. Seeds were treated with different concentrations of EMS and the effect on seed survival is shown. FIG. 1B. Determination of the optimum EMS dose for production of M2 seeds in *N. benthamiana*. Seeds were treated with different concentrations of EMS and the effect on plant fertility was recorded.

Figure 2:
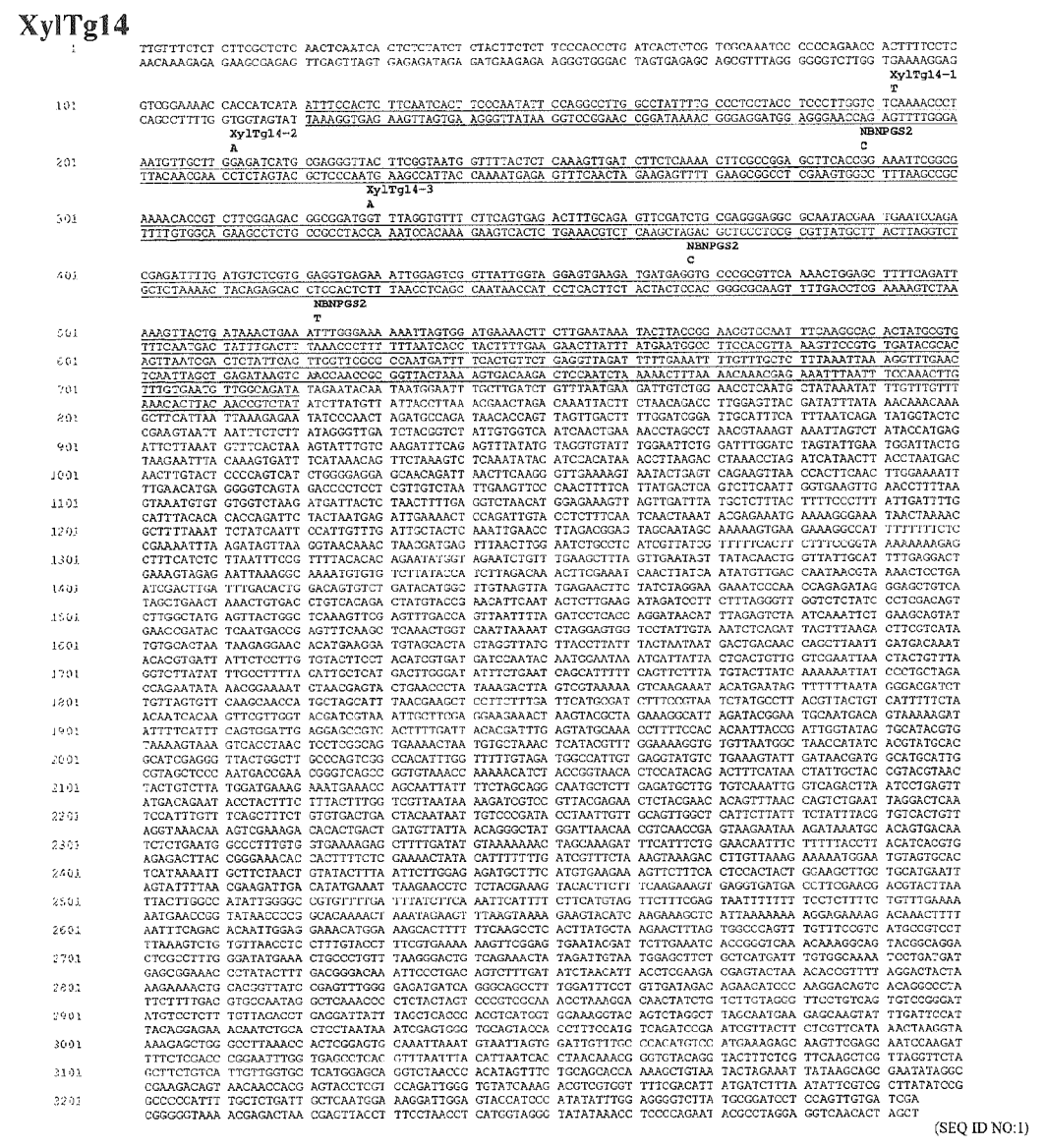

FIG. 2: Summary of the position of SNPs between accessions *BENTHAMIANA* and NBNPGS2 and of mutant alleles in XylTg14 and XylTg19. The SNP and name of allele or accession are indicated above the sequence. The area searched for EMS mutations and/or SNPs is underlined.

Figure 3:
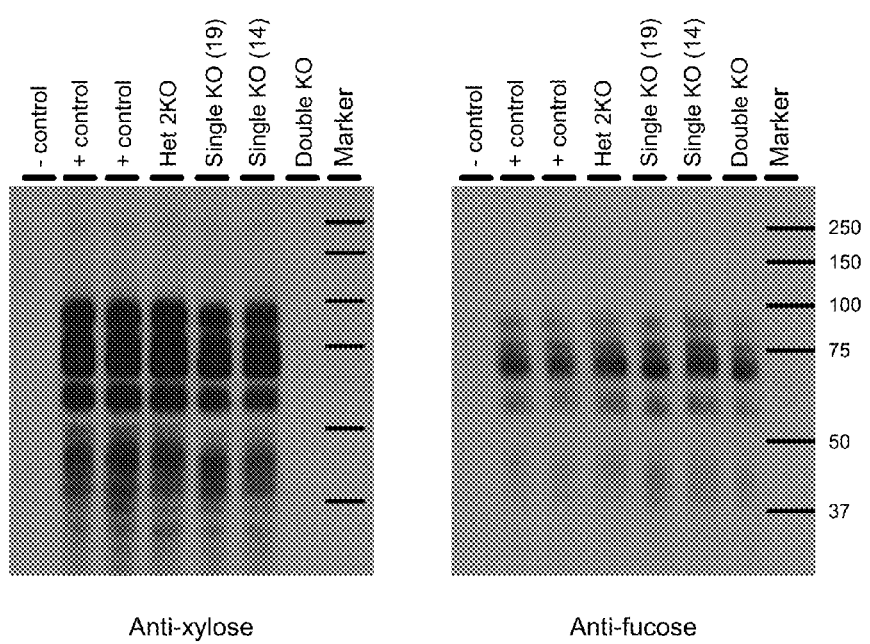

FIG. 3: Absence of detectable beta-1,2-xylose sugars on N-glycans of total protein from plants homozygous for XylTg14-1 and XylTg19-1. Left panel: western blot probed with anti-xylose antibody; right panel: western blot probed with anti-fucose antibody. − (negative) control: no protein loaded; + (positive) control: protein from wt *BENTHAMIANA* accession; Het 2KO: protein from double heterozygous mutant; single KO (14): protein from plant homozygous for XylTg14-1; single KO (19): protein from plant homozygous for XylTg19-1; Double KO: protein from plant homozygous for XylTg14-1 and -19-1. 10 µg total protein was loaded per lane.

Figure 4:
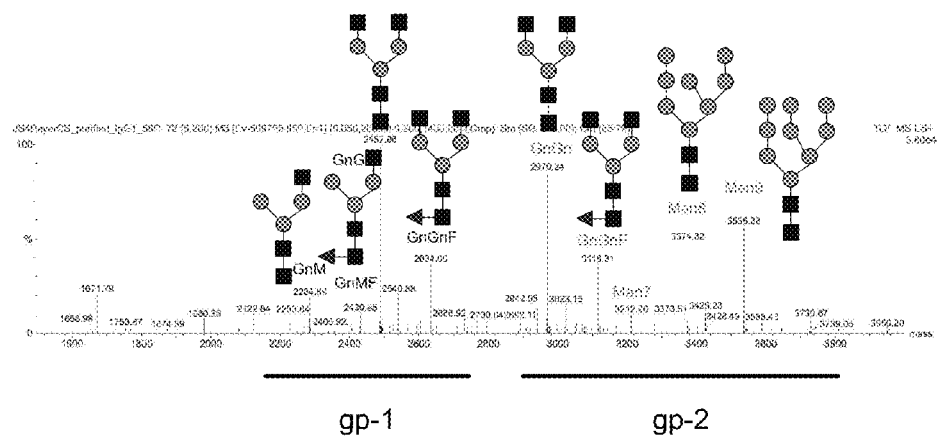

FIG. 4: N-glycan analysis of heavy chain of a magnICON®-expressed IgG1 from a homozygous XylTg14-1 and XylTg19-1 double knock out *N. benthamiana* plant. Purified heavy chain was digested with a proteinase and resulting peptides were analyzed by LC-ESI-MS. Peaks in the mass spectrum representing glyco-peptides were annotated for the type of glycan attached. In this method two glycopeptides are produced as a result of partial inhibition of the proteinase by glycosylation. Therefore, gp-1 and gp-2 refer to a similar heavy chain glycopeptide differing by 1 amino acid. ■=N-acetylglucosamine (Gn), ●=Mannose (Man) and ◀=fucose (F). From the glycan analysis it is apparent that xylose residues are not present on the heterologous glycan structures.

DETAILED DESCRIPTION OF THE INVENTION

*Nicotiana benthamiana* has been described as an amphidiploid species from a hybridization between *Nicotiana debneyi* and *Nicotiana suaveolens* (Goodspeed, T. H. (1954) *The Genus Nicotiana*, Waltham, Mass.: Chronica Botanica). An amphidiploid is a polyploid formed from the union of two separate chromosome sets and their subsequent doubling, thus *N. benthamiana* can also be designated as an allotetraploid species.

The invention provides in a first embodiment a beta-1,2-xylosyltransferase null mutant of the plant *Nicotiana benthamiana*, or cells, parts, seed or progeny thereof, reference seed having been deposited on May 21, 2009 at the NCIMB under accession number NCIMB 41622. In another embodiment the invention provides a beta-1,2-xylosyltransferase null mutant of the plant *Nicotiana benthamiana*, or cells, parts, seed or progeny thereof, obtained from reference seed having been deposited on May 21, 2009 at the NCIMB under accession number NCIMB 41622. In yet another embodiment the invention provides a beta-1,2-xylosyltransferase null mutant of the plant *Nicotiana benthamiana*, or cells, parts, seed or progeny thereof, obtainable by propagation of and/or breeding with a plant grown from the reference seed having been deposited on May 21, 2009 at the NCIMB under accession number NCIMB 41622. It is envisaged that two "alleles" are present in vivo for each beta-1,2-xylosyltransferase gene at each XylT locus in the genome (one allele being the gene sequence found on one chromosome and the other on the homologous chromosome). The nucleotide sequence of these two alleles may be identical (homozygous plant) or different (heterozygous plant) in any given plant, although the number of different possible alleles existing for each XylT gene may be much larger than two in the species population as a whole.

In another embodiment a *Nicotiana benthamiana* beta-1,2-xylosyltransferase null mutant plant or plant cell is provided characterized by having a combination of homozygous null alleles selected from a null allele, from the group consisting of xyltg14-1, xyltg14-2 or xyltg14-3 and a null allele selected from the group consisting of xyltg19-1 or xyltg19-2.

Reference seeds of *Nicotiana benthamiana* plants comprising alleles xyltg14-1 and xyltg19-1 in homozygous state have been deposited at the National Collection of Industrial, Marine and Food Bacteria (NCIMB), NCIMB Ltd, Ferguson Building, Craibstone Estate, Bucksburn, Aberdeen AB219YA, Scotland, on May 21, 2009, under accession number NCIMB 41622 (strain designation 09GNNB000046).

In another embodiment the invention provides *Nicotiana benthamiana* seed characterized as being homozygous for two null alleles, xyltg14-1 and xyltg19-1, of beta-1,2-xylosyltransferase, having been deposited at the NCNB on May 21, 2009, under accession number NCIMB 41622.

In a further embodiment the invention provides a *Nicotiana benthamiana* plant, or a cell, part, seed or progeny thereof, obtained from the seed which has been deposited at the NCNB on May 21, 2009, under accession number NCIMB 41622.

DEFINITIONS

In this invention "seed" refers to any plant structure which is formed by continued differentiation of the ovule of the plant, following its normal maturation point at flower opening, irrespective of whether it is formed in the presence or absence of fertilization and irrespective of whether or not said seed structure is fertile or infertile.

The word "expression" as used herein shall be taken in its widest context to refer to the transcription of a particular genetic sequence to produce sense or antisense mRNA or the translation of a sense mRNA molecule to produce a peptide, polypeptide, oligopeptide, protein or enzyme molecule. In the case of expression comprising the production of a sense mRNA transcript, the word "expression" may also be construed to indicate the combination of transcription and translation processes, with or without subsequent post-translational events which modify the biological activity, cellular or sub-cellular localization, turnover or steady-state level of the peptide, polypeptide, oligopeptide, protein or enzyme molecule.

By "inhibiting, interrupting, knocking-out, knocking-down or otherwise reducing the expression" of a stated integer is meant that transcription and/or translation post-translational modification of the integer is inhibited or prevented or knocked-down or knocked-out or interrupted such that the specified integer has a reduced biological effect on a cell, tissue, organ or organism in which it would otherwise be expressed.

Those skilled in the art will be aware of how whether expression is inhibited, interrupted or reduced, without undue experimentation. For example, the level of expression of a particular gene may be determined by polymerase chain reaction (PCR) following reverse transcription of an mRNA template molecule. Alternatively, the expression level of a genetic sequence may be determined by northern hybridisation analysis or dot-blot hybridisation analysis or in situ hybridisation analysis or similar technique, wherein mRNA is transferred to a membrane support and hybridised to a "probe" molecule which comprises a nucleotide, sequence complementary to the nucleotide sequence of the mRNA transcript encoded by the gene-of-interest, labeled with a suitable reporter molecule such as a radioactively-labelled dNTP (eg [alpha-32P] dCTP or [alpha-35S] dCTP) or biotinylated dNTP, amongst others. Expression of the gene-of-interest may then be determined by detecting the appearance of a signal produced by the reporter molecule bound to the hybridised probe molecule.

Alternatively, the rate of transcription of a particular gene may be determined by nuclear run-on and/or nuclear run-off experiments, wherein nuclei are isolated from a particular cell or tissue and the rate of incorporation of rNTPs into specific mRNA molecules is determined. Alternatively, the expression of the gene-of-interest may be determined by RNase protection assay, wherein a labelled RNA probe or "riboprobe" which is complementary to the nucleotide sequence of mRNA encoded by said gene-of-Interest is annealed to said mRNA for a time and under conditions sufficient for a double-stranded mRNA molecule to form, after which time the sample is subjected to digestion by RNase to remove single-stranded RNA molecules and in particular, to remove excess unhybridised riboprobe. Such approaches are described in detail by Sambrook, J., Fritsch, E. F. and Maniatis, T. *Molecular Cloning: a laboratory manual*. $2^{nd}$ ed. N.Y., Cold Spring Harbor Laboratory, Cold Spring Harbor Laboratory Press, 1989. 1659 p. ISBN 0-87969-309-6.

Those skilled in the art will also be aware of various immunological and enzymatic methods for detecting the level of expression of a particular gene at the protein level, for example using rocket immunoelectrophoresis, ELISA, radio-immunoassay and western blot immunoelectrophoresis techniques, amongst others.

As used herein, the term "allele(s)" means any of one or more alternative forms of a gene at a particular locus. In a diploid (or amphidiploid) cell of an organism, alleles of a given gene are located at a specific location or locus (loci plural) on a chromosome. One allele is present on each chromosome of the pair of homologous chromosomes.

As used herein, the term "heterozygous" means a genetic condition existing when two different alleles reside at a specific locus, but are positioned individually on corresponding pairs of homologous chromosomes in the cell. Conversely, as used herein, the term "homozygous" means a genetic condition existing when two identical alleles reside at a specific locus, but are positioned individually on corresponding pairs of homologous chromosomes in the cell.

Whenever reference to a "plant" or "plants" according to the invention is made, it is understood that also plant parts (cells, tissues or organs, seeds, severed parts such as roots, leaves, flowers, pollen, etc.), progeny of the plants which retain the distinguishing characteristics of the parents, such as seed obtained by selfing or crossing, are encompassed herein, unless otherwise indicated.

"Wild type" (also written "wildtype" or "wild-type"), as used herein, refers to a typical form of a plant or a gene as it most commonly occurs in nature. A "wild type plant" refers to a plant with the most common phenotype of such plant in the natural population. A "wild type allele" refers to an allele of a gene required to produce the wild-type phenotype. By contrast, a "mutant plant" refers to a plant with a different rare phenotype of such plant in the natural population or produced by human intervention, e.g. by mutagenesis, and a "mutant allele" refers to an allele of a gene required to produce the mutant phenotype.

As used herein, the term "wild type beta-1,2-xylosyltransferase" (e.g. wild type XylTg14 or XylTg19), means a naturally occurring XylT allele found within *Nicotiana*, in particular *Nicotiana benthamiana* plants, which encodes a functional XylT protein. A fragment of the XylTg14 gene is depicted in SEQ ID NO: 11 in WO2007107296 and a fragment of the XylTg19 gene is depicted in SEQ ID NO: 13 in WO2007107296. In the present application the nucleotide sequence of a fragment of the XylTg14 gene is in the present application depicted as SEQ ID NO: 1 while the nucleotide sequence of a fragment of the XylTg19 gene is in the present application depicted as SEQ ID NO: 3. In contrast, the term "mutant XylT" (e.g. mutant XylTg14 or XylTg19), as used herein, refers to a XylT allele, which does not encode a functional XylT protein, i.e. a XylT allele encoding a nonfunctional XylT protein, which, as used herein, refers to a XylT protein having no biological activity or encoding no XylT protein at all. Such a "mutant XylT allele" (also herein further designated as "null" allele) is a wild-type XylT allele, which comprises one or more mutations in its nucleic acid sequence, whereby the mutation(s) result in no detectable amount of functional XylT protein in the plant or plant cell in vivo. In a preferred embodiment said mutations in the nucleic acid sequence lead to a STOP codon when said nucleic acid sequence is translated. As used herein, "a beta-1,2-xylosyltransferase null mutant" is a *Nicotiana benthamiana* plant with two XylTg14 null alleles and two XylTg19 null alleles which combination results in a loss of beta-1,2 bound xylose-sugars on endogenous and heterologous produced N-glycan structures of glycoproteins. Mutant alleles of the XylT protein-encoding nucleic acid sequences are designated as "xylt" (e.g. xyltg14-1, xyltg14-2, xyltg14-3 or xyltg19-1, xyltg19-2, respectively) herein.

Allele xyltg14-1 corresponds with a C→T mutation on position 192 in SEQ ID NO: 1, thereby introducing a STOP codon in SEQ ID NO: 1.

Allele xyltg14-2 corresponds with a G→A mutation on position 212 in SEQ ID NO: 1, thereby introducing a STOP codon in SEQ ID NO: 1.

Allele xyltg14-3 corresponds with a G→A mutation on position 329 in SEQ ID NO: 1, thereby introducing a STOP codon in SEQ ID NO: 1.

Allele xyltg19-1 corresponds with a C→T mutation on position 139 in SEQ ID NO: 1, thereby introducing a STOP codon in SEQ ID NO: 3.

Allele xyltg19-2 corresponds with a G→A mutation on position 183 in SEQ ID NO: 1, thereby introducing a STOP codon in SEQ ID NO: 3.

A summary of the identified alleles and possibility of the occurrence of other alleles is depicted in Table 2.

Mutant null alleles can be either "natural mutant" null alleles, which are mutant null alleles found in nature (e.g. produced spontaneously without human application of mutagens) or "induced mutant" null alleles, which are induced by human intervention, e.g. by mutagenesis and are called non-natural mutant null alleles.

A "significantly reduced amount of functional XylT protein" refers to a reduction in the amount of a functional XylT protein produced by the cell comprising a mutant xyltg14 or xyltg19 allele by at least 95% or preferably 100% (i.e. no functional XylT protein is produced by the alleles) as compared to the amount of the functional XylT protein produced by the cell not comprising the mutant XylT alleles. This definition encompasses the production of a "non-functional" XylT protein (e.g. truncated XylT protein) having no biological activity in vivo, the reduction in the absolute amount of the functional XylT protein (e.g. no functional XylT protein being made due to the mutation in the XylT gene).

"Mutagenesis", as used herein, refers to the process in which plant cells (e.g., a plurality of *Nicotiana benthamiana* seeds or other parts, such as pollen, etc.) are subjected to a technique which induces mutations in the DNA of the cells, such as contact with a mutagenic agent, such as a chemical substance (such as ethylmethylsulfonate (EMS), ethylnitrosourea (ENU), etc.) or ionizing radiation (neutrons (such as in fast neutron mutagenesis, etc.), alpha rays, gamma rays (such as that supplied by a Cobalt 60 source), X-rays, UV-radiation, etc.), or a combination of two or more of these. Thus, the desired mutagenesis of one or more XylT alleles may be accomplished by use of chemical means such as by contact of one or more plant tissues with ethylmethylsulfonate (EMS), ethylnitrosourea, etc., by the use of physical means such as x-ray, etc, or by gamma radiation, such as that supplied by a Cobalt 60 source. While mutations created by irradiation are often large deletions or other gross lesions such as translocations or complex rearrangements, mutations created by chemical mutagens are often more discrete lesions such as point mutations. For example, EMS alkylates guanine bases, which results in base mispairing: an alkylated guanine will pair with a thymine base, resulting primarily in G/C to A/T transitions. Following mutagenesis, *Nicotiana benthamiana* plants are regenerated from the treated cells using known techniques. For instance, the resulting *Nicotiana benthamiana* seeds may be planted in accordance with conventional growing procedures and following self-pollination seed is formed on the plants. Additional seed that is formed as a result of such self-pollination in the present or a subsequent generation may be harvested and screened for the presence of mutant XylT alleles. Several techniques are known to screen for specific mutant alleles, e.g., Deleteagene™ (Delete-a-gene; Li et al., 2001, Plant J 27: 235-242) uses polymerase chain reaction (PCR) assays to screen for deletion mutants generated by fast neutron mutagenesis, TILLING (targeted induced local lesions in genomes; McCallum et al., 2000, *Nat Biotechnol* 18:455-457) identifies EMS-induced point mutations, etc. Additional techniques to screen for the presence of specific mutant XylT alleles are described in the Examples below.

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e., a position in an alignment where a residue is present in one sequence but not in the other, is regarded as a position with non-identical residues. The "optimal alignment" of two sequences is found by aligning the two sequences over the entire length according to the Needleman and Wunsch global alignment algorithm (Needleman and Wunsch, 1970, *J Mol Biol* 48(3):443-53) in The European Molecular Biology Open Software Suite (EMBOSS, Rice et al., 2000, *Trends in Genetics* 16(6): 276-277; see e.g. http://www.ebi.ac.uk/emboss/align/index.html) using default settings (gap opening penalty=10 (for nucleotides)/10 (for proteins) and gap extension penalty=0.5 (for nucleotides)/0.5 (for proteins)). For nucleotides the default scoring matrix used is EDNAFULL and for proteins the default scoring matrix is EBLOSUM62.

Nucleic Acid Sequences According to the Invention

Provided are both wild type XylT nucleic acid sequences encoding functional XylT proteins and mutant xylt nucleic acid sequences (comprising one or more mutations, preferably mutations which result in no or a significantly reduced biological activity of the encoded XylT protein or in no XylT protein being produced) of XylT genes from *Nicotiana* species, particularly from *Nicotiana benthamiana*.

Mutant nucleic acid sequences of Xyltg14 and Xyltg19 have been isolated from *Nicotiana benthamiana* as depicted in the sequence listing. The wild type Xyltg14 and Xyltg19 sequences are depicted, while the mutant xyltg14 and xyltg19 sequences of these sequences are described herein below in FIG. 2 and in the examples, with reference to the wild type Xyltg14 and Xyltg19 sequences.

To determine the functionality of a specific Xylt allele/protein in plants, particularly in *Nicotiana benthamiana* plants, the functional level of beta-1,2-xylosyltransferase activity can be determined as described further in the examples. Alternatively Xylt alleles can be incorporated into a transformation vector and be used to transform a knock-out line of the model plant *Arabidopsis thaliana*, with deficiency of active beta-1,2-xylosyltransferase (XylT) and core alpha-1,3-fucosyltransferase (FucT) (Strasser et al. (2004) *FEBS Lett.* 561: 132-136). Complementation of this knock-out line with the particular XylT allele should indicate whether the XylT is allele is functional or whether it is a null allele. Functional complementation as indicated by the presence of xylose-residues on plant or heterologous glycoproteins can be monitored as further shown in the examples.

Methods According to the Invention

Mutant xylt14 and/or xylt19 alleles may be generated (for example induced by mutagenesis) and/or identified using a range of methods, which are conventional in the art, for example using PCR based methods to amplify part or all of the ind genomic or cDNA.

Following mutagenesis, plants are grown from the treated seeds, or regenerated from the treated cells using known techniques. For instance, mutagenized seeds may be planted in accordance with conventional growing procedures and following self-pollination seed is formed on the plants. Additional seed which is formed as a result of such self-pollination in the present or a subsequent generation may be harvested and screened for the presence of mutant XylT alleles, using techniques which are conventional in the art, for example polymerase chain reaction (PCR) based techniques (amplification of the ind alleles) or hybridization based techniques, e.g. Southern blot analysis, BAC library screening, and the like, and/or direct sequencing of xylt alleles. To screen for the presence of point mutations (so called Single Nucleotide Polymorphisms or SNPs) in mutant IND alleles, SNP detection methods conventional in the art can be used, for example oligo-ligation-based techniques, single base extension-based techniques or techniques based on differences in restriction sites, such as TILLING.

As described above, mutagenization (spontaneous as well as induced) of a specific wild-type XylT allele results in the presence of one or more deleted, inserted, or substituted nucleotides (hereinafter called “mutation region”) in the resulting mutant XylT allele. The mutant XylT allele can thus be characterized by the location and the configuration of the one or more deleted, inserted, or substituted nucleotides in the wild type XylT allele. The site in the wild type XylT allele where the one or more nucleotides have been inserted, deleted, or substituted, respectively, is herein also referred to as the “mutation region or sequence”. A “5' or 3' flanking region or sequence” as used herein refers to a DNA region or sequence in the mutant (or the corresponding wild type) XylT allele of at least 20 bp, preferably at least 50 bp, at least 750 bp, at least 1500 bp, and up to 5000 bp of DNA different from the DNA containing the one or more deleted, inserted, or substituted nucleotides, preferably DNA from the mutant (or the corresponding wild type) XylT allele which is located either immediately upstream of and contiguous with (5' flanking region or sequence”) or immediately downstream of and contiguous with (3' flanking region or sequence”) the mutation region in the mutant XylT allele (or in the corresponding wild type XYLT allele). A “joining region” as used herein refers to a DNA region in the mutant (or the corresponding wild type) XylT allele where the mutation region and the 5' or 3' flanking region are linked to each other. A “sequence spanning the joining region between the mutation region and the 5' or 3' flanking region thus comprises a mutation sequence as well as the flanking sequence contiguous therewith.

The tools developed to identify a specific mutant XylT allele or the plant or plant material comprising a specific mutant XylT allele, or products which comprise plant material comprising a specific mutant XylT allele are based on the specific genomic characteristics of the specific mutant XylT allele as compared to the genomic characteristics of the corresponding wild type XylT allele, such as, a specific restriction map of the genomic region comprising the mutation region, molecular markers or the sequence of the flanking and/or mutation regions.

Once a specific mutant XylT allele has been sequenced, primers and probes can be developed which specifically recognize a sequence within the 5' flanking, 3' flanking and/or mutation regions of the mutant XylT allele in the nucleic acid (DNA or RNA) of a sample by way of a molecular biological technique. For instance a PCR method can be developed to identify the mutant XylT allele in biological samples (such as samples of plants, plant material or products comprising plant material). Such a PCR is based on at least two specific “primers”: one recognizing a sequence within the 5' or 3' flanking region of the mutant XylT allele and the other recognizing a sequence within the 3' or 5' flanking region of the mutant XylT allele, respectively; or one recognizing a sequence within the 5' or 3' flanking region of the mutant XylT allele and the other recognizing a sequence within the mutation region of the mutant XylT allele; or one recognizing a sequence within the 5' or 3' flanking region of the mutant XylT allele and the other recognizing a sequence spanning the joining region between the 3' or 5' flanking region and the mutation region of the specific mutant XylT allele (as described further below), respectively.

The primers preferably have a sequence of between 15 and 35 nucleotides which under optimized PCR conditions “specifically recognize” a sequence within the 5' or 3' flanking region, a sequence within the mutation region, or a sequence spanning the joining region between the 3' or 5' flanking and mutation regions of the specific mutant XylT allele, so that a specific fragment (“mutant XylT specific fragment” or discriminating amplicon) is amplified from a nucleic acid sample comprising the specific mutant XylT allele. This means that only the targeted mutant XylT allele, and no other sequence in the plant genome, is amplified under optimized PCR conditions.

Detection and/or identification of a “mutant XylT specific fragment” can occur in various ways, e.g., via size estimation after gel or capillary electrophoresis or via fluorescence-based detection methods. The mutant XylT specific fragments may also be directly sequenced. Other sequence specific methods for detection of amplified DNA fragments are also known in the art.

Standard PCR protocols are described in the art, such as in ‘PCR Applications Manual” (Roche Molecular Biochemicals, 2nd Edition, 1999) and other references. The optimal conditions for the PCR, including the sequence of the specific primers, is specified in a “PCR identification protocol” for each specific mutant XylT allele. It is however understood that a number of parameters in the PCR identification protocol may need to be adjusted to specific laboratory conditions, and may be modified slightly to obtain similar results. For instance, use of a different method for preparation of DNA may require adjustment of, for instance, the amount of primers, polymerase, MgCl$_2$ concentration or annealing conditions used. Similarly, the selection of other primers may dictate other optimal conditions for the PCR identification protocol. These adjustments will however be apparent to a person skilled in the art, and are furthermore detailed in current PCR application manuals such as the one cited above.

Yet other possibilities of PCR identification protocols to identify specific mutant XylT alleles are described in the Examples section.

Alternatively, specific primers can be used to amplify a mutant XylT specific fragment that can be used as a "specific probe" for identifying a specific mutant XylT allele in biological samples. Contacting nucleic acid of a biological sample, with the probe, under conditions that allow hybridization of the probe with its corresponding fragment in the nucleic acid, results in the formation of a nucleic acid/probe hybrid. The formation of this hybrid can be detected (e.g. labeling of the nucleic acid or probe), whereby the formation of this hybrid indicates the presence of the specific mutant XylT allele. Such identification methods based on hybridization with a specific probe (either on a solid phase carrier or in solution) have been described in the art. The specific probe is preferably a sequence that, under optimized conditions, hybridizes specifically to a region within the 5' or 3' flanking region and/or within the mutation region of the specific mutant XylT allele (hereinafter referred to as "mutant XylT specific region"). Preferably, the specific probe comprises a sequence of between 10 and 1000 bp, 50 and 600 bp, between 100 to 500 bp, between 150 to 350 bp, which is at least 80%, preferably between 80 and 85%, more preferably between 85 and 90%, especially preferably between 90 and 95%, most preferably between 95% and 100% identical (or complementary) to the nucleotide sequence of a specific region. Preferably, the specific probe will comprise a sequence of about 13 to about 100 contiguous nucleotides identical (or complementary) to a specific region of the specific mutant XylT allele.

In yet another embodiment the invention provides a *Nicotiana benthamiana* plant which is a double, homozygous null mutant for beta-1,2-xylosyltransferase further comprising a silenced alpha-1,3-fucosyltransferase activity.

The level of alfa(1,3) fucosyltransferase activity can be conveniently reduced or eliminated by transcriptional or post-transcriptional silencing of the expression of an endogenous alfa(1,3) fucosyltransferase encoding gene. To this end a silencing RNA molecule is introduced in the plant cells targeting the endogenous alfa(1,3) fucosyltransferase encoding gene. As used herein, "silencing RNA" or "silencing RNA molecule" refers to any RNA molecule, which upon introduction into a plant cell, reduces the expression of a target gene. Such silencing RNA may e.g. be so-called "antisense RNA", whereby the RNA molecule comprises a sequence of at least 20 consecutive nucleotides having 95% sequence identity to the complement of the sequence of the target nucleic acid, preferably the coding sequence of the target gene. However, antisense RNA may also be directed to regulatory sequences of target genes, including the promoter sequences and transcription termination and polyadenylation signals. Silencing RNA further includes so-called "sense RNA" whereby the RNA molecule comprises a sequence of at least 20 consecutive nucleotides having 95% sequence identity to the sequence of the target nucleic acid. Other silencing RNA may be "unpolyadenylated RNA" comprising at least 20 consecutive nucleotides having 95% sequence identity to the complement of the sequence of the target nucleic acid, such as described in WO01/12824 or U.S. Pat. No. 6,423,885 (both documents herein incorporated by reference). Yet another type of silencing RNA is an RNA molecule as described in WO03/076619 (herein incorporated by reference) comprising at least 20 consecutive nucleotides having 95% sequence identity to the sequence of the target nucleic acid or the complement thereof, and further comprising a largely-double stranded region as described in WO03/076619 (including largely double stranded regions comprising a nuclear localization signal from a viroid of the Potato spindle tuber viroid-type or comprising CUG trinucleotide repeats). Silencing RNA may also be double stranded RNA comprising a sense and antisense strand as herein defined, wherein the sense and antisense strand are capable of base-pairing with each other to form a double stranded RNA region (preferably the said at least 20 consecutive nucleotides of the sense and antisense RNA are complementary to each other). The sense and antisense region may also be present within one RNA molecule such that a hairpin RNA (hpRNA) can be formed when the sense and antisense region form a double stranded RNA region. hpRNA is well-known within the art (see e.g WO99/53050, herein incorporated by reference). The hpRNA may be classified as long hpRNA, having long, sense and antisense regions which can be largely complementary, but need not be entirely complementary (typically larger than about 200 bp, ranging between 200-1000 bp). hpRNA can also be rather small ranging in size from about 30 to about 42 bp, but not much longer than 94 bp (see WO04/073390, herein incorporated by reference). Silencing RNA may also be artificial micro-RNA molecules as described e.g. in WO2005/052170, WO2005/047505 or US 2005/0144667 (all documents incorporated herein by reference)

In another embodiment, the silencing RNA molecules are provided to the plant cell or plant by producing a transgenic plant cell or plant comprising a chimeric gene capable of producing a silencing RNA molecule, particularly a double stranded RNA ("dsRNA") molecule, wherein the complementary RNA strands of such a dsRNA molecule comprises a part of a nucleotide sequence encoding a XylT or FucT protein.

The enzyme that catalyses the transfer of fucose from GDP-fucose to the core β-linked N-acetyl glucosamine (GlcNAc) of protein-bound N-glycans is α-1,3-fucosyltransferase ("FucT", EC 2.4.1.214).

Genes encoding alfa(1,3) fucosyltransferase (FucT) in plants are well known and include the following database entries identifying experimentally demonstrated and putative FucT cDNA and gene sequences, parts thereof or homologous sequences: NM 112815 (*Arabidopsis thaliana*), NM103858 (*Arabidopsis thaliana*), AJ 618932 (*Physcomitrella patens*) At1g49710 (*Arabidopsis thaliana*) and At3g19280 (*Arabidopsis thaliana*). DQ789145 (*Lemna minor*), AY557602 (*Medicago truncatula*) Y18529 (*Vigna radiata*) AP004457 (*Oryza sativa*), AJ891040 encoding protein CAI70373 (*Populus alba×Populus tremula*) AY082445 encoding protein AAL99371 (*Medicago sativa*) AJ582182 encoding protein CAE46649 (*Triticum aestivum*) AJ582181 encoding protein CAE46648 (*Hordeum vulgare*) (all sequences herein incorporated by reference).

Based on the available sequences, the skilled person can isolate genes encoding alfa(1,3) fucosyltransferase or genes encoding beta(1,2) xylosyltransferase from plants other than the plants mentioned above. Homologous nucleotide sequence may be identified and isolated by hybridization under stringent conditions using as probes identified nucleotide sequences.

"Stringent hybridization conditions" as used herein means that hybridization will generally occur if there is at least 95% and preferably at least 97% sequence identity between the probe and the target sequence. Examples of stringent hybridization conditions are overnight incubation in a solution comprising 50% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared carrier DNA such as salmon sperm DNA, followed by washing the hybridization support in 0.1×SSC at approximately 65° C., preferably twice for about 10 minutes. Other hybridization and wash conditions are well known and are exemplified in Sambrook et al, Molecular Cloning: A Laboratory Manual, Second Edition, Cold Spring Harbor, N.Y. (1989), particularly chapter 11.

Nucleotide sequences obtained in this way should be verified for encoding a polypeptide having an amino acid sequence which is at least 80% to 95% identical to a known alfa(1,3) fucosyltransferase from plants.

In yet another embodiment the beta-1,2-xylosyltransferase null mutant *Nicotiana benthamiana* plant which comprises a silenced alfa(1,3) fucosyltransferase additionally comprises a beta-1,4-galactosyltransferase activity. Conveniently, such activity may be introduced into plant cells by providing them with a chimeric gene comprising a plant-expressible promoter operably linked to a DNA region encoding a beta(1,4) galactosyltransferase and optionally a 3' end region involving in transcription termination and polyadenylation functional in plant cells. The term "beta-1,4-galactosyltransferase" refers to the glycosyltransferase designated as EC2.4.1.38 that is required for the biosynthesis of the backbone structure from type 2 chain (Galbeta1→4GlcNAc), which appears widely on N-linked glycans, i.e., which enzyme has galactosylating activity on N-linked glycans. Useful beta-1,4-galactosyltransferases are derived from human, mouse, rat as well as orthologs of beta-1,4-galactosyltransferase from non-mammalian species such as chicken and zebrafish (see also WO2008125972).

Regions encoding a beta-1,4-galactosyltransferase are preferably obtained from mammalian organisms, including humans, but may be obtained from other organisms as well. NM022305 (*Mus musculus*) NM146045 (*Mus musculus*) NM 004776 (*Homo sapiens*) NM 001497 (*Homo sapiens*) are a few database entries for genes encoding a β(1,4) galactosyltransferase. Others database entries for β(1,4) galactosyltransferases include AAB05218 (*Gallus gallus*), XP693272 (*Danio rerio*), CAF95423 (*Tetraodon nigroviridis*) or NP001016664 (*Xenopus tropicalis*) (all sequence herein incorporated by reference).

As used herein, the term "plant-expressible promoter" means a DNA sequence that is capable of controlling (initiating) transcription in a plant cell. This includes any promoter of plant origin, but also any promoter of non-plant origin which is capable of directing transcription in a plant cell, i.e., certain promoters of viral or bacterial origin such as the CaMV35S (Harpster et al. (1988) *Mol Gen Genet.* 212(1): 182-90, the subterranean clover virus promoter No 4 or No 7 (WO9606932), or T-DNA gene promoters but also tissue-specific or organ-specific promoters including but not limited to seed-specific promoters (e.g., WO89/03887), organ-primordia specific promoters (An et al. (1996) *Plant Cell* 8(1): 15-30), stem-specific promoters (Keller et al., (1988) *EMBO J.* 7(12): 3625-3633), leaf specific promoters (Hudspeth et al. (1989) *Plant Mol Biol.* 12: 579-589), mesophyl-specific promoters (such as the light-inducible Rubisco promoters), root-specific promoters (Keller et al. (1989) *Genes Dev.* 3: 1639-1646), tuber-specific promoters (Keil et al. (1989) *EMBO J.* 8(5): 1323-1330), vascular tissue specific promoters (Peleman et al. (1989) *Gene* 84: 359-369), stamen-selective promoters (WO 89/10396, WO 92/13956), dehiscence zone specific promoters (WO 97/13865) and the like.

In yet another embodiment the mutant *Nicotiana benthamiana* plants comprising a silenced fucosyltransferase and optionally a further beta-1,4-galactosyltransferase can comprise also a heterologous gene encoding a glycoprotein. The glycoproteins may be glycoproteins endogeneous to the cell of the higher plant, and may result in altered functionality, folding or half-life of these proteins. Glycoproteins also include proteins which are foreign to the cell of the higher plant (i.e. a heterologous glycoprotein), i.e. which are not normally expressed in such plant cells in nature. These may include mammalian or human proteins, which can be used as therapeutics such as e.g. monoclonal antibodies. Conveniently, the foreign glycoproteins may be expressed from chimeric genes comprising a plant-expressible promoter and the coding region of the glycoprotein of interest, whereby the chimeric gene is stably integrated in the genome of the plant cell. Methods to express foreign proteins in plant cells are well known in the art. Alternatively, the foreign glycoproteins may also be expressed in a transient manner, e.g. using the viral vectors and methods described in WO02/088369, WO2006/079546 and WO2006/012906 or using the viral vectors described in WO89/08145, WO93/03161 and WO96/40867 or WO96/12028.

By "heterologous protein" it is understood a protein (i.e. a polypeptide) that is not expressed by the plant or plant cells in nature. This is in contrast with a homologous protein which is a protein naturally expressed by a plant or plant cell. Heterologous and homologous polypeptides that undergo post-translational N-glycosylation are referred to herein as heterologous or homologous glycoproteins.

Examples of heterologous proteins of interest that can be advantageously produced by the methods of this invention include, without limitation, cytokines, cytokine receptors, growth factors (e.g. EGF, HER-2, FGF-alpha, FGF-beta, TGF-alpha, TGF-beta, PDGF, IGF-I, IGF-2, NGF), growth factor receptors. Other examples include growth hormones (e.g. human growth hormone, bovine growth hormone); insulin (e.g., insulin A chain and insulin B chain), pro-insulin, erythropoietin (EPO), colony stimulating factors (e.g. G-CSF, GM-CSF, M-CSF); interleukins; vascular endothelial growth factor (VEGF) and its receptor (VEGF-R), interferons, tumor necrosis factor and its receptors, thrombopoietin (TPO), thrombin, brain natriuretic peptide (BNP); clotting factors (e.g. Factor VIII, Factor IX, von Willebrands factor and the Ike), anti-clotting factors; tissue plasminogen activator (TPA), urokinase, follicle stimulating hormone (FSH), luteinizing hormone (LH), calcitonin, CD proteins (e.g., CD2, CD3, CD4, CD5, CD7, CD8, CDI Ia, CDI Ib, CD18, CD19, CD20, CD25, CD33, CD44, CD45, CD71, etc.), CTLA proteins (e.g. CTLA4); T-cell and B-cell receptor proteins, bone morphogenic proteins (BNPs, e.g. BMP-I, BMP-2, BMP-3, etc.), neurotrophic factors, e.g. bone derived neurotrophic factor (BDNF), neurotrophins, e.g. rennin, rheumatoid factor, RANTES, albumin, relaxin, macrophage inhibitory protein (e.g. MIP-I, MIP-2), viral proteins or antigens, surface membrane proteins, on channel proteins, enzymes, regulatory proteins, immunomodulatory proteins, (e.g. HLA, MHC, the B7 family), homing receptors, transport proteins, superoxide dismutase (SOD), G-protein coupled receptor proteins (GPCRs), neuromodulatory proteins, Alzheimer's Disease associated proteins and peptides. Fusion proteins and polypeptides, chimeric proteins and polypeptides, as well as fragments or portions, or mutants, variants, or analogs of any of the aforementioned proteins and polypeptides are also included among the suitable proteins, polypeptides and peptides that can be produced by the methods of the present invention. In a preferred embodiment, the protein of interest is a glycoprotein. One class of glycoproteins are viral glycoproteins, in particular subunits, than can be used to produce for example a vaccine. Some examples of viral proteins comprise proteins from rhinovirus, poliomyelitis virus, herpes virus, bovine herpes virus, influenza virus, newcastle disease virus, respiratory syncitio virus, measles virus, retrovirus, such as human immunodeficiency virus or a parvovirus or a papovavirus, rotavirus or a coronavirus, such as transmissable gastroenteritisvirus or a flavivirus, such as tick-borne encephalitis virus or yellow fever virus, a togavirus, such as rubella virus or eastern-, western-, or venezuelean equine encephalomyelitis virus, a hepatitis causing virus, such as hepatitis A or hepatitis B virus, a pestivirus, such as hog cholera virus or a rhabdovirus, such as rabies virus. In another preferred embodiment, the heterologous glycoprotein is an antibody or a fragment thereof. The term "antibody" refers to recombinant antibodies (for example of the classes IgD, IgG, IgA, IgM, IgE) and recombinant antibodies such as single-chain antibodies, chimeric and humanized antibodies and multi-specific antibodies. The term "antibody" also refers to fragments and derivatives of all of the foregoing, and may further comprises any modified or derivatised variants thereof that retain the ability to specifically bind an epitope. Antibody derivatives may comprise a protein or chemical moiety conjugated to an antibody. A monoclonal antibody is capable of selectively binding to a target antigen or epitope. Antibodies include, monoclonal antibodies (mAbs), humanized or chimeric antibodies, camelized antibodies, camelid antibodies (Nanobodies®), single chain antibodies (scFvs), Fab fragments, F(ab')$_2$ fragments, disulfide-linked Fvs (sdFv) fragments, anti-idiotypic (anti-Id) antibodies, intra-bodies, synthetic antibodies, and epitope-binding fragments of any of the above. The term "antibody" also refers to fusion protein that includes a region equivalent to the Fc region of an immunoglobulin. Also envisaged is the production in the plant or plant cells of the invention of so called dual-specificity antibodies (Bostrom J et al (2009) *Science* 323, 1610-1614).

Preferred antibodies within the scope of the present invention include those comprising the amino acid sequences of the following antibodies: anti-HER2 antibodies including antibodies comprising the heavy and light chain variable regions (see U.S. Pat. No. 5,725,856) or Trastuzumab such as HERCEPTIN™; anti-CD20 antibodies such as chimeric anti-CD20 as in U.S. Pat. No. 5,736,137, a chimeric or humanized variant of the 2H7 antibody as in U.S. Pat. No. 5,721,108; anti-VEGF antibodies including humanized and/or affinity matured anti-VEGF antibodies such as the humanized anti-VEGF antibody huA4.6.1 AVASTIN™ (WO 96/30046 and WO 98/45331); anti-EGFR (chimerized or humanized antibody as in WO 96/40210); anti-CD3 antibodies such as OKT3 (U.S. Pat. No. 4,515,893); anti-CD25 or anti-tac antibodies such as CHI-621 (SIMULECT) and (ZENAPAX) (U.S. Pat. No. 5,693,762). The present invention provides a method for the production of an antibody which comprises culturing a transformed plant cell or growing a transformed plant of the present invention. The produced antibody may be purified and formulated in accordance with standard procedures.

The nucleotide sequences of the glycosyltransferases and/or the heterologous genes may be codon optimized to increase the level of expression within the plant. By codon optimization it is meant the selection of appropriate DNA nucleotides for the synthesis of oligonucleotide building blocks, and their subsequent enzymatic assembly, of a structural gene or fragment thereof in order to approach codon usage in plants.

In certain embodiments methods for obtaining a desired glycoprotein or functional fragment thereof comprise cultivating a plant described herein until said plant has reached a harvestable stage, harvesting and fractionating the plant to obtain fractionated plant material and at least partly isolating said glycoprotein from said fractionated plant material.

In certain embodiments methods for obtaining a desired glycoprotein or functional fragment thereof comprise growing recombinant plant cells in cell culture in a fermentor until said cell culture has reached a harvestable stage or the desired glycoprotein can be collected from the medium. The glycoproteins described herein, such as e.g., antibodies, vaccines, cytokines and hormones, may be purified by standard techniques well known to those of skill in the art. Such recombinantly produced proteins may be directly expressed or expressed as a fusion protein. The recombinant protein is purified by a combination of cell lysis (e.g., sonication, French press) and affinity chromatography or other affinity-based method. For fusion products, subsequent digestion of the fusion protein with an appropriate proteolytic enzyme releases the desired recombinant protein.

In yet another embodiment the invention provides a method to produce at least one heterologous protein in null mutant *Nicotiana benthamiana* plants described herein before comprising the steps of: a) providing a null mutant plant or plant cell according to the invention with at least one chimeric gene comprising the following operably linked nucleic acid molecules: i) plant-expressible promoter, ii) DNA region encoding a heterologous protein, and iii) DNA region involved in transcription termination and polyadenylation, and b) cultivating said plant or plant cell and isolating said at least one heterologous protein from said plant or plant cell. In a preferred embodiment the heterologous protein produced is an antibody.

The proteins described herein, recombinant or synthetic, may be purified to substantial purity by standard techniques well known in the art, including detergent solubilization, selective precipitation with such substances as ammonium sulfate, column chromatography, immunopurification methods, and others. See, for instance, R. Scopes, Protein Purification: Principles and Practice, Springer-Verlag: New York (1982); Deutscher, Guide, to Protein Purification, Academic Press (1990). For example, antibodies may be raised to the proteins as described herein. Purification from *E. coli* can be achieved following procedures described in U.S. Pat. No. 4,511,503. The protein may then be isolated from cells expressing the protein and further purified by standard protein chemistry techniques as described herein. Detection of the expressed protein is achieved by methods known in the art and include, for example, radioimmunoassays, Western blotting techniques or immunoprecipitation.

Throughout the description and Examples, reference is made to the following sequences:

SEQ ID NO 1: nucleotide sequence of beta-1,2-xylosyl-transferase XylTg14 of *Nicotiana benthamiana*
SEQ ID NO 2: amino acid sequence of SEQ ID NO: 1
SEQ ID NO 3: nucleotide sequence of beta-1,2-xylosyl-transferase XylTg19 of *Nicotiana benthamiana*
SEQ ID NO 4: amino acid sequence of SEQ ID NO: 3

EXAMPLES

1. Determination of the Optimal EMS Dosage for M2 Seed Production

The optimum dose for EMS mutagensis was determined by treating seeds of *N. benthamiana* with 0, 50, 75, 100, 150, and 200 mM EMS. Briefly, seeds were imbibed for 2 hours at room temperature, treated with EMS for 4 hours at room temperature and washed 5 times for 15 minutes at room temperature. Seeds were dried overnight and sown immediately. The effects on germination, seedling lethality and plant fertility were recorded. *N. benthamiana* has been described to be an amphidiploid species from a combination of *N. debneyi* and *N. suaveolens* (Goodspeed, T. H. (1954) The genus *Nicotiana*, Waltham, Mass.: *Chronica Botanica*). Surprisingly, we discovered that the parents, being diploids, proved to be more resistant to EMS as compared to *N. benthamiana*, being a tetraploid. Results for the *N. benthamiana* seeds are shown in FIGS. 1A and 1B. Although EMS treatment caused a delay in germination, no lethality was detected up to 75 mM EMS. At higher EMS doses, lethality rose quickly and at 150 mM EMS no seeds survived the treatment (FIG. 1A). Fertility already was affected at 50 mM. By treating the seeds with 75 mM approximately 60% of the M1 plants were infertile (FIG. 1B). Based on these results, the optimum EMS dose was set at 75 mM.

2. SNP Detection by Direct Sequencing

EMS-induced point mutations were detected in a high-throughput manner by direct sequence analysis by using the method described in Smits B. M. et al (2006) *Pharmacogenet. Genomics* 16: 159-169. Briefly, specific gene fragments were amplified by PCR from DNA of leaf tissue of individual plants using gene specific primers. Each primer carried an additional sequence at its 5' end that allowed analysis of the sequence of both strands of the resulting PCR fragment. In a first step we optimized the method. Thereto DNA was extracted from several *N. benthamiana* accessions (see Table 1 for the accessions). The first exons of genes XylTg14 and XylTg19 were amplified and nucleotide sequences were determined. The chromatograms of sequences were analyzed for Single Nucleotide Polymorphisms (SNPs) by comparing them to the XylTg14 and XylTg19 sequences in NovoSNP (Weckx S. et al. (2005) *Genome Research* 15:436-442). It appeared that only accession NBNPGS2 from the USDA National Germplasm System (accession code P1555684) contained several SNPs compared to the *N. benthamiana* accession used in our research (i.e. Cultivar "*BENTHAMIANA*" supplied by Icon Genetics GmbH). The position of the identified SNPs are summarized in FIG. 2.

Accession NBNPGS2 was used as a control and position marker (i.e. leaf material from NBNPGS2 was sampled in well H12) when sampling leaf material, in 96-well format, for DNA production of the final M2 populations.

TABLE 1

*N. benthamiana* accessions used in the testing and production of EMS-mutagenized M2 population.

| CULTIVAR NAME | SUPPLIER | SUPPLIER CODE | seed lot number | protocol name |
|---|---|---|---|---|
| *BENTHAMIANA* | Icon Genetics | | 05GANB000001 | |
| NBNIJM1 | University of Nijmegen | A34750397 | 06GNNB000004 | 06GNNB002 |
| NBNIJM2 | University of Nijmegen | 964750110 | 06GNNB000005 | 06GNNB002 |
| NBNIJM2 | University of Nijmegen | 964750110 | 06GNNB000007 | 06GNNB003 |
| NBNIJM2 | University of Nijmegen | 964750110 | 06GNNB000008 | 06GNNB003 |
| NBNIJM2 | University of Nijmegen | 964750110 | 06GNNB000009 | 06GNNB003 |
| NBVIENNA1 | University of Vienna | | 06GNNB000006 | 06GNNB003 |
| NBNPGS1 | USDA, National Plant Germplasm System | PI555478 | 06GNNB000010 | 06GNNB006 |
| NBNPGS2 | USDA, National Plant Germplasm System | PI555684 | 06GNNB000011 | 06GNNB006 |
| NBALTADIS | Altadis, Institut du Tabac | *N. BENTHAMIANA* G | 06GNNB000012 | 06GNNB011 |
| NBTRCF1 | AusPGRIS—Australian Plant Genetic Resource Information Service | AusTRCF303915 | 06GNNB000013 | 06GNNB011 |
| NBTRCF2 | AusPGRIS—Australian Plant Genetic Resource Information Service | AusTRCF303916 | 06GNNB000014 | 06GNNB011 |

Accession *BENTHAMIANA* was used for the final M2 populations.
The other accessions were merely used for testing and optimizing the SNP detection method.
Accession NBNPGS2 was used as a control in each 96-well plate in sampling the final M2 populations.

3. Defining the Target Area for Mutagenesis Detection

Because the SNP detection by direct sequencing, was limited to sequence fragments of 500 bp, is was necessary to identify a 500 bp region in the XylTg14 and XylTg19 genes that had the highest chance producing a null mutation when mutagenized with EMS. Therefore we needed to identify a region that: (1) had the highest density of codons that can change into stop codons by one G to A or C to T mutation and/or splice donor and acceptor sites, and (2) was placed in or upstream of a catalytic or conserved domain. In order to find the highest density of candidate stop or splice mutations, we used EmsPred; a proprietary algorithm to Bayer Bio-Science that identifies all codons in a coding sequence that can be mutated to a stop codon or a splice mutant induced by EMS mutagenesis. The positions identified in XylTg14 and XylTg19 are listed in Table 2. For the identification of a region upstream of a catalytic domain, we used a publication by Pagny et al. (Pagny, S. et al (2003) *Plant J.* 33:189-203) which describes the inactivation of *A. thaliana* β-1,2-xylosyltransferase by the removal of 82, 106, and 143 amino acids at the N-terminus. In conclusion, we decided to search for putative null mutations between positions 120 and 720 of both XylTg14 and XylTg19. In XylTg14, this area corresponds to a part of the first exon (until position 650) and part of the first intron and codes for amino acids 41 to 217. In XylTg19, this area also corresponds to part of the first exon (until position 648) and part of the first intron and codes for amino acids 41 to 216.

TABLE 2

Summary of all positions in XylTg14 and -19 that produce stop or splice mutations by one EMS mutation. The positions of the stop codons of the final XylTg14 and -19 alleles are also indicated.

| position | base | type | allele |
|---|---|---|---|
| XylTg14 | | | |
| 84 | C | stop | |
| 144 | C | stop | |
| 160 | G | stop | |
| 161 | G | stop | |
| 187 | G | stop | |
| 188 | G | stop | |
| 192 | C | stop | XylTg14-1 |
| 211 | G | stop | |
| 212 | G | stop | XylTg14-2 |
| 328 | G | stop | |
| 329 | G | stop | XylTg14-3 |
| 357 | C | stop | |
| 387 | C | stop | |
| 495 | C | stop | |
| 618 | C | stop | |
| 653 | G | splice | |
| 654 | G | splice | |
| 1913 | G | splice | |
| 1915 | G | stop | |
| 1916 | G | stop | |
| 1944 | C | stop | |
| 1984 | C | stop | |
| 1985 | G | stop | |
| 2063 | G | splice | |
| 2064 | G | splice | |
| 2608 | G | splice | |
| 2612 | C | stop | |
| 2628 | G | stop | |
| 2629 | G | stop | |
| 2784 | G | stop | |
| 2785 | G | stop | |
| 2786 | C | stop | |
| 2870 | C | stop | |
| 2960 | C | stop | |
| 2984 | C | stop | |
| 3009 | G | stop | |
| 3010 | G | stop | |
| 3080 | C | stop | |
| 3086 | C | stop | |
| 3095 | C | stop | |
| 3224 | C | stop | |
| 3228 | G | stop | |
| 3229 | G | stop | |
| XylTg19 | | | |
| 79 | C | stop | |
| 139 | C | stop | XylTg19-1 |
| 155 | G | stop | |
| 156 | G | stop | |
| 182 | G | stop | |
| 183 | G | stop | XylTg19-2 |
| 187 | C | stop | |
| 206 | G | stop | |
| 207 | G | stop | |
| 323 | G | stop | |
| 324 | G | stop | |
| 352 | C | stop | |
| 382 | C | stop | |
| 490 | C | stop | |
| 613 | C | stop | |
| 652 | G | splice | |
| 653 | G | splice | |
| 2198 | G | splice | |
| 2196 | G | stop | |
| 2197 | G | stop | |
| 2225 | C | stop | |
| 2265 | G | stop | |

TABLE 2-continued

Summary of all positions in XylTg14 and -19 that produce stop or splice mutations by one EMS mutation. The positions of the stop codons of the final XylTg14 and -19 alleles are also indicated.

| position | base | type | allele |
|---|---|---|---|
| 2266 | G | stop | |
| 2344 | G | splice | |
| 2345 | G | splice | |
| 2888 | G | splice | |
| 2892 | C | stop | |
| 2908 | G | stop | |
| 2909 | G | stop | |
| 3064 | G | stop | |
| 3065 | G | stop | |
| 3066 | C | stop | |
| 3150 | C | stop | |
| 3240 | C | stop | |
| 3289 | G | stop | |
| 3290 | G | stop | |
| 3360 | C | stop | |
| 3366 | C | stop | |
| 3375 | C | stop | |
| 3504 | C | stop | |
| 3508 | G | stop | |
| 3509 | G | stop | |

4. Identification of XylTg14 and XylTg19 Single Knock Plants and Generation of Double Knock Put Plants In total, 5700 M2 individuals were screened for mutations in XylTg14 and 6200 for XylTg19. Three putative null alleles were identified in XylTg14, at nucleotide positions 192, 212, and 392, labeled XylTg14-1, -2, and -3, respectively. Two putative null alleles were identified in XylTg19, at nucleotide positions 139 and 183, labeled XylTg19-1 and -2, respectively (FIG. 2 and Table 2).

In order to retrieve homozygous mutants for these mutations, 24 plants from the original M2 seed lot—in which the mutation had been identified—were grown, sampled, and analyzed for the specific mutation by direct sequencing. Mutants xyltg14-1 were crossed with xyltg19-1 to produce heterozygous double mutants. In addition, all mutants (i.e. including xyltg14-2 and xyltg14-3 and xyltg19-2) were allowed to self fertilize to establish homozygous single mutant seed lots.

Progeny from the XylTg14-1×XylTg19-1 crosses were analyzed by direct sequencing to confirm their heterozygous genotype and selected plants were allowed to self-fertilize. Double homozygous mutants were identified from the progeny of these plants by direct sequencing. To establish a stable homozygous seed lot, these plants were allowed to self-fertilize. Simultaneously, these plants were backcrossed with the BENTHAMIANA accession to produce start producing a plant homozygous for xyltg14-1 and xyltg19-1 but free of undesired background mutations.

5. Glycan Analysis of XylTg14 and XylTg19 Single and Double Mutants

To determine whether the mutations found in alleles XylTg14-1 and -19-1 cause inactivation of the XylTg14 and -19 genes respectively, a western blot was performed on total protein from different heterozygous and homozygous single and double mutants. 10 μg total protein was loaded per lane, blotted and probed with either anti-xylose or anti-fucose antibodies as produced by the method described by Faye et al. (Faye, L. et al (1993) *Anal. Biochem.* 209:104-108). FIG. 3 shows that total protein of the double homozygous mutant is not recognized by the anti-xylose antibody. In contrast, protein from either single homozygous mutants or double heterozygous mutants is recognized by the anti-xylose antibody. The control blot probed with the anti-fucose antibody shows that protein was loaded in all lanes. Together this shows that the mutations in alleles xyltg14-1 and xyltg19-1 are null mutations and that generating null mutants of both XylTg14 and XylTg19, for instance in the double homozygous xyltg14-1 and xyltg19-1 plants, is both sufficient and necessary to inactivate the complete β1,2-xylosyltransferase activity and to fully prevent addition of any β1,2-xylose to the N-glycans of *N. benthamiana*.

In a next step we investigated the presence or absence of xylose sugars on N-glycans of a heterologous glycoprotein produced in the xyltg14-1 and xyltg19-1 homozygous *N. benthamiana* plant. Thereto, we analyzed the N-glycans present on the heavy chain of an IgG1 expressed in a double knock out plant using magnICON® (Marillonnet et al. (2005) *Nature Biotechnology* 23, 718-723). Nine days after infiltration, total protein was extracted from the mutant plant and IgG1 was purified using protein G. The heavy chain of the purified antibody was isolated by cutting the corresponding band from a reducing SDS-PAGE. The heavy chain protein in this band was used for glycan analysis by LC-MS as described by Kolarich et al. (Kolarich, D. et al (2006) *Proteomics* 6:3369-3380). Results shown in FIG. 4 show that no xylose is present on the heavy chain of this IgG1. This confirms that the double homozygous xyltg14-1 and xyltg19-1 *N. benthamiana* mutant completely lacks beta-1,2-xylosyltransferase activity.

---

The invention claimed is:

1. A beta-1,2-xylosyltransferase null mutant of a *Nicotiana benthamiana* plant, or cells, parts, seed or progeny thereof, obtained by breeding with reference seed having been deposited on May 21, 2009 at the NCIMB under accession number NCIMB 41622, wherein said null mutant of *Nicotiana benthamiana*, or cells, parts, seed, or progeny thereof comprises null alleles XylTg14-1 and XylTg19-1 as defined in FIG. 2 in homozygous state.

2. The plant or plant cell of claim 1, which does not form beta-1,2-xylosyl-sugars on N-glycan structures of glycoproteins produced in said plant.

3. A *Nicotiana benthamiana* seed characterized as being homozygous for two null alleles, XylTg14-1 and XylTg19-1, of beta-1,2-xylosyltransferase, having been deposited at the NCIMB on May 21, 2009, under accession number NCIMB 41622.

4. A *Nicotiana benthamiana* plant, or a cell, part, seed or progeny thereof, obtained from the seed of claim 3, wherein said plant, part, seed, or progeny is homozygous for the two null alleles XylTg14-1 and XylTg19-1 of beta-1,2-xylosyltransferase.

5. The plant or plant cell of claim 1, further comprising a silenced alpha-1,3-fucosyltransferase activity.

6. The plant or plant cell of claim 5, further comprising a chimeric gene encoding beta-1,4-galactosyltransferase activity.

7. The plant or plant cell of claim 1, further comprising a chimeric gene encoding a heterologous protein.

8. A method to produce at least one heterologous protein in plants or plant cells according to claim 1, comprising the steps of:
   a. providing a plant or plant cell according to claim 1 with at least one chimeric gene comprising the following operably linked nucleic acid molecules:
      a. a plant-expressible promoter,
      b. a DNA region encoding a heterologous protein,
      c. a DNA region involved in transcription termination and polyadenylation, and
   b. cultivating said plant or plant cell and isolating said at least one heterologous protein from said plant or plant cell.

9. The plant or plant cell of claim 4, further comprising a silenced alpha-1,3-fucosyltransferase activity.

10. The plant or plant cell of claim 4, further comprising a chimeric gene encoding beta-1,4-galactosyltransferase activity.

11. The plant or plant cell of claim 4, further comprising a chimeric gene encoding a heterologous protein.

* * * * *

SEQUENCE LISTING

```
<160> NUMBER OF SEQ ID NOS: 4

<210> SEQ ID NO 1
<211> LENGTH: 3294
<212> TYPE: DNA
<213> ORGANISM: Nicotiana benthamiana
<220> FEATURE:
<221> NAME/KEY: CDS
<222> LOCATION: (3)..(653)
<220> FEATURE:
<221> NAME/KEY: Intron
<222> LOCATION: (654)..(1913)
<220> FEATURE:
<221> NAME/KEY: CDS
<222> LOCATION: (1914)..(2063)
<220> FEATURE:
<221> NAME/KEY: Intron
<222> LOCATION: (2064)..(2608)
<220> FEATURE:
<221> NAME/KEY: CDS
<222> LOCATION: (2609)..(3286)

<400> SEQUENCE: 1 tt gtt tct ctc ttc gct ctc aac tca atc act ctc tat ctc tac ttc       47
   Val Ser Leu Phe Ala Leu Asn Ser Ile Thr Leu Tyr Leu Tyr Phe
   1               5                   10                  15 tct tcc cac cct gat cac tct cgt cgc aaa tcc ccc cag aac cac ttt       95
Ser Ser His Pro Asp His Ser Arg Arg Lys Ser Pro Gln Asn His Phe
                20                  25                  30 tcc tcg tcg gaa aac cac cat cat aat ttc cac tct tca atc act tcc      143
Ser Ser Ser Glu Asn His His His Asn Phe His Ser Ser Ile Thr Ser
            35                  40                  45 caa tat tcc agg cct tgg cct att ttg ccc tcc tac ctc cct tgg tct      191
Gln Tyr Ser Arg Pro Trp Pro Ile Leu Pro Ser Tyr Leu Pro Trp Ser
        50                  55                  60 caa aac cct aat gtt gct tgg aga tca tgc gag ggt tac ttc ggt aat      239
Gln Asn Pro Asn Val Ala Trp Arg Ser Cys Glu Gly Tyr Phe Gly Asn
    65                  70                  75 ggt ttt act ctc aaa gtt gat ctt ctc aaa act tcg ccg gag ctt cac      287
Gly Phe Thr Leu Lys Val Asp Leu Leu Lys Thr Ser Pro Glu Leu His
80                  85                  90                  95 cgg aaa ttc ggc gaa aac acc gtc ttc gga gac ggc gga tgg ttt agg      335
Arg Lys Phe Gly Glu Asn Thr Val Phe Gly Asp Gly Gly Trp Phe Arg
                100                 105                 110 tgt ttc ttc agt gag act ttg cag agt tcg atc tgc gag gga ggc gca      383
Cys Phe Phe Ser Glu Thr Leu Gln Ser Ser Ile Cys Glu Gly Gly Ala
            115                 120                 125 ata cga atg aat cca gac gag att ttg atg tct cgt gga ggt gag aaa      431
Ile Arg Met Asn Pro Asp Glu Ile Leu Met Ser Arg Gly Gly Glu Lys
        130                 135                 140
```

| | |
|---|---|
| ttg gag tcg gtt att ggt agg agt gaa gat gat gag gtg ccc gcg ttc<br>Leu Glu Ser Val Ile Gly Arg Ser Glu Asp Asp Glu Val Pro Ala Phe<br>145 150 155 | 479 |
| aaa act gga gct ttt cag att aaa gtt act gat aaa ctg aaa ttt ggg<br>Lys Thr Gly Ala Phe Gln Ile Lys Val Thr Asp Lys Leu Lys Phe Gly<br>160 165 170 175 | 527 |
| aaa aaa tta gtg gat gaa aac ttc ttg aat aaa tac tta ccg gaa ggt<br>Lys Lys Leu Val Asp Glu Asn Phe Leu Asn Lys Tyr Leu Pro Glu Gly<br>180 185 190 | 575 |
| gca att tca agg cac act atg cgt gag tta atc gac tct att cag ttg<br>Ala Ile Ser Arg His Thr Met Arg Glu Leu Ile Asp Ser Ile Gln Leu<br>195 200 205 | 623 |
| gtt ggc gcc aat gat ttt cac tgt tct gag gttagatttt tgaaattttg<br>Val Gly Ala Asn Asp Phe His Cys Ser Glu<br>210 215 | 673 |
| tttgctcttt aaattaaagg tttgaacttt gtgaatgttg cagatatag aatacaataa | 733 |
| tggaatttgc ttgatctgtt taatgaagat tgtctggaac tcaatgcta taaatatttg | 793 |
| tttgtttgct tcattaatta agagaatat cccaactaga tgccagataa caccagttag | 853 |
| ttgacttttg gatcggattg catttcattt aatcagatat ggtactcatt cttaaatgtt | 913 |
| tcactaaagt atttgtcaag atttcagagt ttatatgtag gtgtatttgg aattctggat | 973 |
| ttggatctag tattgaatgg attactgaac ttgtactccc cagtcatctg gggaggagca | 1033 |
| acagattaac ttcaagggtt gaaaagtaat actgagtcag aagttaacca cttcaacttg | 1093 |
| gaaaattgta atgtgtgtg gtctaagatg attactctaa cttttgaggt ctaacatgga | 1153 |
| gaaagttagt tgatttatgc tctttactt tccctttatt gattttggct tttaaattct | 1213 |
| atcaattcca ttgtttgatt gctactcaaa ttgaaccta gacggagtag caatagcaaa | 1273 |
| aagtgaagaa aggccatttt ttttctcctt tcatctctta atttccgttt tacacacaga | 1333 |
| atatggtaga atctgtttga agctttagtt gaatagttat acaactggtt attgcatttt | 1393 |
| gaggactatc gacttgattt gacactggac agtgtctgat acatggcttg taagttatga | 1453 |
| gaacttctat ctaggaagaa atcccaacca gagataggga gctgtcactt ggctatgagt | 1513 |
| tactggctca aagttcgagt ttgaccagtt aatttttagat cctcaccagg ataacattta | 1573 |
| gagtctaatc aaattctgaa gcagtattgt gcactaataa gaggaacaca tgaaggatgt | 1633 |
| agcactacta ggttatgtta ccttatttac taataatgac tgacaaccag cttaattgat | 1693 |
| gacaaatggt cttatatttg ccttttacat tgctcatgac ttgggatatt tctgaatcag | 1753 |
| cattttcag ttcttatgt acttatcaaa aaattatccc tgctagatgt tagtgttcaa | 1813 |
| gcaaccatgc tagcatttaa cgaagctcct tctttgattc atgcgatctt ccgtaatct | 1873 |
| atgccttacg ttactgtcat ttttctaatt ttcatttcag tgg att gag gag ccg<br>Trp Ile Glu Glu Pro<br>220 | 1928 |
| tca ctt ttg att aca cga ttt gag tat gca aac ctt ttc cac aca att<br>Ser Leu Leu Ile Thr Arg Phe Glu Tyr Ala Asn Leu Phe His Thr Ile<br>225 230 235 | 1976 |
| acc gat tgg tat agt gca tac gtg gca tcg agg gtt act ggc ttg ccc<br>Thr Asp Trp Tyr Ser Ala Tyr Val Ala Ser Arg Val Thr Gly Leu Pro<br>240 245 250 | 2024 |
| agt cgg cca cat ttg gtt ttt gta gat ggc cat tgt gag gtatgtctga<br>Ser Arg Pro His Leu Val Phe Val Asp Gly His Cys Glu<br>255 260 265 | 2073 |
| aagtattgat aacgatggca tgcatttac tgtcttatgg atgaaagaaa tgaaaccagc | 2133 |
| aattattttc tagcaggcaa tgctcttgag atgcttgtgt caaattggtc agacttaatc | 2193 |

```
ctgagtttcc atttgtttca gctttctgtg tgactgacta caataattgt cccgatacct    2253
aattgttgca gttggctcat tcttatttct atttacgtgt cactgtttct ctgaatggcc    2313
ctttgtggtg aaaagagctt tgatatgta aaaaaactag caaagatttc atttctggaa    2373
caatttcttt ttaccttaca tcacgtgtca taaaattgct tctaactgta tactttaatt    2433
cttggagaga tgctttcatg tgaagaaagt tctttcactc cactactgga agcttgctgc    2493 atgaattta cttggccata ttggggccgt gttttgattt atcttcaaat tcattttctt    2553
catgtagttc tttcgagtaa ttttttttcc tcttttctgt ttgaaaaaat ttcag aca     2611
                                                                Thr caa ttg gag gaa aca tgg aaa gca ctt ttt tca agc ctc act tat gct      2659
Gln Leu Glu Glu Thr Trp Lys Ala Leu Phe Ser Ser Leu Thr Tyr Ala
    270             275                 280 aag aac ttt agt ggc cca gtt tgt ttc cgt cat gcc gtc ctc tcg cct      2707
Lys Asn Phe Ser Gly Pro Val Cys Phe Arg His Ala Val Leu Ser Pro
285             290                 295                 300 ttg gga tat gaa act gcc ctg ttt aag gga ctg tca gaa act ata gat      2755
Leu Gly Tyr Glu Thr Ala Leu Phe Lys Gly Leu Ser Glu Thr Ile Asp
                305                 310                 315 tgt aat gga gct tct gct cat gat ttg tgg caa aat cct gat gat aag      2803
Cys Asn Gly Ala Ser Ala His Asp Leu Trp Gln Asn Pro Asp Asp Lys
            320                 325                 330 aaa act gca cgg tta tcc gag ttt ggg gag atg atc agg gca gcc ttt      2851
Lys Thr Ala Arg Leu Ser Glu Phe Gly Glu Met Ile Arg Ala Ala Phe
        335                 340                 345 gga ttt cct gtt gat aga cag aac atc cca agg aca gtc aca ggc cct      2899
Gly Phe Pro Val Asp Arg Gln Asn Ile Pro Arg Thr Val Thr Gly Pro
    350                 355                 360 aat gtc ctc ttt gtt aga cgt gag gat tat tta gct cac cca cgt cat      2947
Asn Val Leu Phe Val Arg Arg Glu Asp Tyr Leu Ala His Pro Arg His
365                 370                 375                 380 ggt gga aag gta cag tct agg ctt agc aat gaa gag caa gta ttt gat      2995
Gly Gly Lys Val Gln Ser Arg Leu Ser Asn Glu Glu Gln Val Phe Asp
                385                 390                 395 tcc ata aag agc tgg gcc tta aac cac tcg gag tgc aaa tta aat gta      3043
Ser Ile Lys Ser Trp Ala Leu Asn His Ser Glu Cys Lys Leu Asn Val
            400                 405                 410 att agt gga ttg ttt gcc cac atg tcc atg aaa gag caa gtt cga gca      3091
Ile Ser Gly Leu Phe Ala His Met Ser Met Lys Glu Gln Val Arg Ala
        415                 420                 425 atc caa gat gct tct gtc att gtt ggt gct cat gga gca ggt cta acc      3139
Ile Gln Asp Ala Ser Val Ile Val Gly Ala His Gly Ala Gly Leu Thr
    430                 435                 440 cac ata gtt tct gca gca cca aaa gct gta ata cta gaa att ata agc      3187
His Ile Val Ser Ala Ala Pro Lys Ala Val Ile Leu Glu Ile Ile Ser
445                 450                 455                 460 agc gaa tat agg cgc ccc cat ttt gct ctg att gct caa tgg aaa gga      3235
Ser Glu Tyr Arg Arg Pro His Phe Ala Leu Ile Ala Gln Trp Lys Gly
                465                 470                 475 ttg gag tac cat ccc ata tat ttg gag ggg tct tat gcg gat cct cca      3283
Leu Glu Tyr His Pro Ile Tyr Leu Glu Gly Ser Tyr Ala Asp Pro Pro
            480                 485                 490 gtt gtgatcga                                                         3294
Val

<210> SEQ ID NO 2
<211> LENGTH: 493
<212> TYPE: PRT
<213> ORGANISM: Nicotiana benthamiana
```

```
<400> SEQUENCE: 2

Val Ser Leu Phe Ala Leu Asn Ser Ile Thr Leu Tyr Leu Tyr Phe Ser
1               5                   10                  15

Ser His Pro Asp His Ser Arg Arg Lys Ser Pro Gln Asn His Phe Ser
                20                  25                  30

Ser Ser Glu Asn His His His Asn Phe His Ser Ser Ile Thr Ser Gln
            35                  40                  45

Tyr Ser Arg Pro Trp Pro Ile Leu Pro Ser Tyr Leu Pro Trp Ser Gln
        50                  55                  60

Asn Pro Asn Val Ala Trp Arg Ser Cys Glu Gly Tyr Phe Gly Asn Gly
65                  70                  75                  80

Phe Thr Leu Lys Val Asp Leu Leu Lys Thr Ser Pro Glu Leu His Arg
                85                  90                  95

Lys Phe Gly Glu Asn Thr Val Phe Gly Asp Gly Trp Phe Arg Cys
            100                 105                 110

Phe Phe Ser Glu Thr Leu Gln Ser Ser Ile Cys Glu Gly Gly Ala Ile
            115                 120                 125

Arg Met Asn Pro Asp Glu Ile Leu Met Ser Arg Gly Gly Glu Lys Leu
    130                 135                 140

Glu Ser Val Ile Gly Arg Ser Glu Asp Asp Glu Val Pro Ala Phe Lys
145                 150                 155                 160

Thr Gly Ala Phe Gln Ile Lys Val Thr Asp Lys Leu Lys Phe Gly Lys
                165                 170                 175

Lys Leu Val Asp Glu Asn Phe Leu Asn Lys Tyr Leu Pro Glu Gly Ala
            180                 185                 190

Ile Ser Arg His Thr Met Arg Glu Leu Ile Asp Ser Ile Gln Leu Val
        195                 200                 205

Gly Ala Asn Asp Phe His Cys Ser Glu Trp Ile Glu Glu Pro Ser Leu
    210                 215                 220

Leu Ile Thr Arg Phe Glu Tyr Ala Asn Leu Phe His Thr Ile Thr Asp
225                 230                 235                 240

Trp Tyr Ser Ala Tyr Val Ala Ser Arg Val Thr Gly Leu Pro Ser Arg
                245                 250                 255

Pro His Leu Val Phe Val Asp Gly His Cys Glu Thr Gln Leu Glu Glu
            260                 265                 270

Thr Trp Lys Ala Leu Phe Ser Ser Leu Thr Tyr Ala Lys Asn Phe Ser
        275                 280                 285

Gly Pro Val Cys Phe Arg His Ala Val Leu Ser Pro Leu Gly Tyr Glu
    290                 295                 300

Thr Ala Leu Phe Lys Gly Leu Ser Glu Thr Ile Asp Cys Asn Gly Ala
305                 310                 315                 320

Ser Ala His Asp Leu Trp Gln Asn Pro Asp Asp Lys Lys Thr Ala Arg
                325                 330                 335

Leu Ser Glu Phe Gly Glu Met Ile Arg Ala Ala Phe Gly Phe Pro Val
            340                 345                 350

Asp Arg Gln Asn Ile Pro Arg Thr Val Thr Gly Pro Asn Val Leu Phe
        355                 360                 365

Val Arg Arg Glu Asp Tyr Leu Ala His Pro Arg His Gly Gly Lys Val
    370                 375                 380

Gln Ser Arg Leu Ser Asn Glu Glu Gln Val Phe Asp Ser Ile Lys Ser
385                 390                 395                 400

Trp Ala Leu Asn His Ser Glu Cys Lys Leu Asn Val Ile Ser Gly Leu
                405                 410                 415
```

```
Phe Ala His Met Ser Met Lys Glu Gln Val Arg Ala Ile Gln Asp Ala
            420                 425                 430

Ser Val Ile Val Gly Ala His Gly Ala Gly Leu Thr His Ile Val Ser
        435                 440                 445

Ala Ala Pro Lys Ala Val Ile Leu Glu Ile Ile Ser Ser Glu Tyr Arg
450                 455                 460

Arg Pro His Phe Ala Leu Ile Ala Gln Trp Lys Gly Leu Glu Tyr His
465                 470                 475                 480

Pro Ile Tyr Leu Glu Gly Ser Tyr Ala Asp Pro Val
                485                 490

<210> SEQ ID NO 3
<211> LENGTH: 3574
<212> TYPE: DNA
<213> ORGANISM: Nicotiana benthamiana
<220> FEATURE:
<221> NAME/KEY: CDS
<222> LOCATION: (7)..(648)
<220> FEATURE:
<221> NAME/KEY: Intron
<222> LOCATION: (649)..(2194)
<220> FEATURE:
<221> NAME/KEY: CDS
<222> LOCATION: (2195)..(2344)
<220> FEATURE:
<221> NAME/KEY: Intron
<222> LOCATION: (2345)..(2888)
<220> FEATURE:
<221> NAME/KEY: CDS
<222> LOCATION: (2889)..(3566)

<400> SEQUENCE: 3
```

| | | | | | | | | | | | | | | | | |
|---|---|---|---|---|---|---|---|---|---|---|---|---|---|---|---|---|
| cacctt | gtt | tct | ctc | ttc | gct | ctc | aac | tca | atc | act | ctc | tat | ctc | tac | | 48 |
| | Val | Ser | Leu | Phe | Ala | Leu | Asn | Ser | Ile | Thr | Leu | Tyr | Leu | Tyr | | |
| | 1 | | | 5 | | | | | 10 | | | | | | | |
| ttc | tct | tcc | cac | cct | gat | cac | aaa | tcc | ccc | caa | aac | cac | ttt | tcc | ttg | 96 |
| Phe | Ser | Ser | His | Pro | Asp | His | Lys | Ser | Pro | Gln | Asn | His | Phe | Ser | Leu | |
| 15 | | | | 20 | | | | | 25 | | | | | 30 | | |
| tcg | gaa | aac | cac | cat | cat | aat | ttc | cac | tct | tca | atc | act | tct | caa | tat | 144 |
| Ser | Glu | Asn | His | His | His | Asn | Phe | His | Ser | Ser | Ile | Thr | Ser | Gln | Tyr | |
| | | | | 35 | | | | | 40 | | | | | 45 | | |
| tcc | aag | cct | tgg | cct | att | ttg | ccc | tcc | tac | ctc | cct | tgg | tct | caa | aac | 192 |
| Ser | Lys | Pro | Trp | Pro | Ile | Leu | Pro | Ser | Tyr | Leu | Pro | Trp | Ser | Gln | Asn | |
| | | 50 | | | | | 55 | | | | | 60 | | | | |
| cct | aat | gtt | gct | tgg | aga | tcg | tgc | gag | ggt | tac | ttc | ggt | aat | ggg | ttt | 240 |
| Pro | Asn | Val | Ala | Trp | Arg | Ser | Cys | Glu | Gly | Tyr | Phe | Gly | Asn | Gly | Phe | |
| | 65 | | | | | 70 | | | | | 75 | | | | | |
| act | ctc | aaa | gtt | gac | ctt | ctc | aaa | act | tcg | ccg | gag | ttt | cac | cgg | aaa | 288 |
| Thr | Leu | Lys | Val | Asp | Leu | Leu | Lys | Thr | Ser | Pro | Glu | Phe | His | Arg | Lys | |
| 80 | | | | | 85 | | | | | 90 | | | | | | |
| ttc | ggc | gat | aac | acc | gtc | tcc | ggt | gac | ggc | gga | tgg | ttt | agg | tgt | ttt | 336 |
| Phe | Gly | Asp | Asn | Thr | Val | Ser | Gly | Asp | Gly | Gly | Trp | Phe | Arg | Cys | Phe | |
| 95 | | | | 100 | | | | | 105 | | | | | | 110 | |
| ttc | agt | gag | act | ttg | cag | agt | tcg | atc | tgc | gag | gga | ggc | gca | ata | cga | 384 |
| Phe | Ser | Glu | Thr | Leu | Gln | Ser | Ser | Ile | Cys | Glu | Gly | Gly | Ala | Ile | Arg | |
| | | | | 115 | | | | | 120 | | | | | 125 | | |
| atg | aat | ccg | gac | gat | att | ttg | atg | tct | cgt | gga | ggt | gag | aaa | ttg | gag | 432 |
| Met | Asn | Pro | Asp | Asp | Ile | Leu | Met | Ser | Arg | Gly | Gly | Glu | Lys | Leu | Glu | |
| | | 130 | | | | | 135 | | | | | 140 | | | | |
| tcg | gtt | att | ggt | agg | aat | gaa | gat | gat | gag | ctg | ccc | atg | ttc | aaa | aat | 480 |
| Ser | Val | Ile | Gly | Arg | Asn | Glu | Asp | Asp | Glu | Leu | Pro | Met | Phe | Lys | Asn | |
| | 145 | | | | | 150 | | | | | 155 | | | | | |

| | |
|---|---|
| gga gct ttc caa att gaa gtt act gat aaa ctg aaa att ggg aaa aaa<br>Gly Ala Phe Gln Ile Glu Val Thr Asp Lys Leu Lys Ile Gly Lys Lys<br>160                        165                    170 | 528 |
| cta gtg gat aaa aaa ttc ttg aat aaa tac tta ccg gga ggt gcg att<br>Leu Val Asp Lys Lys Phe Leu Asn Lys Tyr Leu Pro Gly Gly Ala Ile<br>175                        180                    185                    190 | 576 |
| tca agg cac act atg cgt gag tta att gac tct att cag ttg gtt ggc<br>Ser Arg His Thr Met Arg Glu Leu Ile Asp Ser Ile Gln Leu Val Gly<br>                    195                    200                    205 | 624 |
| gcc gat gaa ttt cac tgt tct gag gttagatttt gatatttatt tgatctttaa<br>Ala Asp Glu Phe His Cys Ser Glu<br>                    210 | 678 |
| attagaggtt tgaactttgt taatgttggc agatatggaa tacaataatg gattttgttt | 738 |
| gatctgttta atgaagattg tctaaaacct caatgctata atatttgtt tgtttgcttc | 798 |
| attaattaaa gagaatatcc cgactagatg ccagataaca ccagttagtt gacttttgga | 858 |
| ttgggttgca tttcatttaa tcagatatgg tactcattct taaatgtttc actaaagaat | 918 |
| ttgtcaagat ttcagagttt atatataggt gtatttggaa ttctggattt ggatctagta | 978 |
| ttgaatggat tactgaattt gtactcccca gtcatcaggg gaggagcaat agatcgaatt | 1038 |
| caagggttga aaagtaatac tgagtcagaa attaaccact ttaacttgga aacggtaaat | 1098 |
| gtatgtgttc taagatgatt attcctataa cttttgatgt ctaatatgga aaagtgagt | 1158 |
| tgatttatgc ttttttccttt tcccttttatt gatgttggtt tttaaattct atcaattcct | 1218 |
| ttgtttggtt gctactcaaa ttgaacctta gacggagtag caatagcaaa aagtgaagaa | 1278 |
| aggacatttt tttctccttt catctcttta tttccgtttg acatacagaa tacggtagca | 1338 |
| tctgcctgaa gtggttaatt tcattcctta aaatttgcat aactaatatt tccgtttttg | 1398 |
| tttttgttta tcttttccat tggcatgcca tgttattttt ggtttaggtt tacataatta | 1458 |
| tttatgtgat ttctgatgga gttactaatg atttttgtt tttgttttg tttttttctt | 1518 |
| ttcctttcc tgagtcgagg gtcgattgga aatagcctct ctgccctttt ggatagggggt | 1578 |
| aaggcctggg tacgtgtacc atccccagac ccactctgt gggactatac cgggtagttg | 1638 |
| ttgttgttgt aattcgagta aatgcctttt gaacctttag ttgaatagtt gtacaactgg | 1698 |
| ttgttgcatt ttgaggacta tcgacttgat ttgacacttt acatgaaaac tttatctag | 1758 |
| gaagaaatcc ctaccagaga tagggagctg tcgcttggtt atgagctact ggcttaaagt | 1818 |
| ttgagtttga cctattaatt ttagatcttc accaggataa catctagagt ttaattaaat | 1878 |
| tctcaagcag tattttgcac taataagggg aacacatgaa ggatgtagca ctactacgtt | 1938 |
| atgttcttta tttactattg attgacaacc agcttaaatg atgacaaatg gtcttatatt | 1998 |
| tgcttttta cattgctcat gacttgggat attttttgaat caacattttt cggttctta | 2058 |
| tgtacttatc aaaaaattat ccctgctaga tgttagtgtt caagcaacat gctagctttt | 2118 |
| aaggaagctc cttcttgat tcatgccatc tttccgaagc cttacgtttc tgtcattttt | 2178 |
| ctaattttca tttcag tgg gtt gag gag ccg tca ctt ttg att aca cga ttt<br>                                  Trp Val Glu Glu Pro Ser Leu Leu Ile Thr Arg Phe<br>                                    215                    220                    225 | 2230 |
| gag tat gca aac ctt ttc cac aca gtt acc gat tgg tat agt gca tac<br>Glu Tyr Ala Asn Leu Phe His Thr Val Thr Asp Trp Tyr Ser Ala Tyr<br>230                        235                    240 | 2278 |

```
gcg gca tcc agg gtt act ggt ttg ccc agt cgg cca aat ttg gtt ttt        2326
Ala Ala Ser Arg Val Thr Gly Leu Pro Ser Arg Pro Asn Leu Val Phe
        245                 250                 255 gta gat ggc cat tgt gag gtatgtttga cagtattgat aacgatggca               2374
Val Asp Gly His Cys Glu
    260 tgcattgtac tgtgttatgg atgaaagaaa tgaaaccatc aattattttc tagtaggcaa      2434 tgctcttaag atgcttgtgt caaattggtt agagttaatc ctaagtttcc atttgtttga      2494 gctttctgtt tgactgacta caatacttgt cccaatacct agttgttgcg gttggctcat      2554 tcttacttct atttacgtgt cactgtttct ctgaatggtc cctttgtggt gaaaagagct      2614 tttgctatgt agaaaaacta gcaaagattt catttctgga gcaacttatt tttaccttac     2674 atcacgtctc ataaaattgc ttctaactgt atactttaat tcttggagag atgctttcat     2734 gtgaataaag ttctttcact ccactactgg aagcttgctg catgaaattt acttggccat    2794 actggggccg tgttttgatt tgtcttcaaa ttcatttttct tcatgtagtt ctttcgagta    2854 atatttttttc ctcttctgtt tgaaaaaaat tcag aca caa ttg gag gaa aca tgg    2909
                                     Thr Gln Leu Glu Glu Thr Trp
                                         265                 270 aaa gca ctt ttt tca agc ctc act tat gct aag aac ttt agt ggc cca        2957
Lys Ala Leu Phe Ser Ser Leu Thr Tyr Ala Lys Asn Phe Ser Gly Pro
        275                 280                 285 gtt tgt ttc cgt cat gct gtc ctc tcg cct tta gga tat gaa act gcc        3005
Val Cys Phe Arg His Ala Val Leu Ser Pro Leu Gly Tyr Glu Thr Ala
        290                 295                 300 ctg ttt aag gga ctg tca gaa act ata gat tgt aat gga gct tct gct        3053
Leu Phe Lys Gly Leu Ser Glu Thr Ile Asp Cys Asn Gly Ala Ser Ala
305                 310                 315 cat gat ttg tgg caa aag cct gat gat aaa aaa act gca cgg ttg tcc        3101
His Asp Leu Trp Gln Lys Pro Asp Asp Lys Lys Thr Ala Arg Leu Ser
320                 325                 330                 335 gag ttt ggg gag atg atc agg gca gcc ttt gga ttt cct gtg gat aga        3149
Glu Phe Gly Glu Met Ile Arg Ala Ala Phe Gly Phe Pro Val Asp Arg
            340                 345                 350 cag aac atc cca agg aca gtc aca ggc cct aat gtc ctc ttt gtt aga        3197
Gln Asn Ile Pro Arg Thr Val Thr Gly Pro Asn Val Leu Phe Val Arg
            355                 360                 365 cgt gag gat tat tta gct cac cca cgt cat ggt gga aag gta cag tct        3245
Arg Glu Asp Tyr Leu Ala His Pro Arg His Gly Gly Lys Val Gln Ser
        370                 375                 380 agg ctt agc aat gaa gag cta gta ttt gat tcc ata aag agc tgg gcc        3293
Arg Leu Ser Asn Glu Glu Leu Val Phe Asp Ser Ile Lys Ser Trp Ala
385                 390                 395 ttg aac cac tcg gag tgt aaa tta aat gta att aac gga ttg ttt gcc        3341
Leu Asn His Ser Glu Cys Lys Leu Asn Val Ile Asn Gly Leu Phe Ala
400                 405                 410                 415 cac atg tcc atg aaa gag caa gtt cga gca atc caa gat gct tct gtc        3389
His Met Ser Met Lys Glu Gln Val Arg Ala Ile Gln Asp Ala Ser Val
            420                 425                 430 att gtt ggt gct cat gga gca ggt cta act cac ata gtt tct gca gca        3437
Ile Val Gly Ala His Gly Ala Gly Leu Thr His Ile Val Ser Ala Ala
            435                 440                 445 cca aaa gct gta ata cta gaa att ata agc agc gaa tat agg cgc ccc        3485
Pro Lys Ala Val Ile Leu Glu Ile Ile Ser Ser Glu Tyr Arg Arg Pro
        450                 455                 460
```

```
cat ttt gct ctg att gca caa tgg aaa gga ttg gag tac cat ccc ata    3533
His Phe Ala Leu Ile Ala Gln Trp Lys Gly Leu Glu Tyr His Pro Ile
465                 470                 475 tat ttg gag ggg tct tat gcg gat cct cca gtt gtgatcga               3574
Tyr Leu Glu Gly Ser Tyr Ala Asp Pro Pro Val
480                 485                 490

<210> SEQ ID NO 4
<211> LENGTH: 490
<212> TYPE: PRT
<213> ORGANISM: Nicotiana benthamiana

<400> SEQUENCE: 4

Val Ser Leu Phe Ala Leu Asn Ser Ile Thr Leu Tyr Leu Tyr Phe Ser
1               5                   10                  15

Ser His Pro Asp His Lys Ser Pro Gln Asn His Phe Ser Leu Ser Glu
            20                  25                  30

Asn His His Asn Phe His Ser Ser Ile Thr Ser Gln Tyr Ser Lys
        35                  40                  45

Pro Trp Pro Ile Leu Pro Ser Tyr Leu Pro Trp Ser Gln Asn Pro Asn
    50                  55                  60

Val Ala Trp Arg Ser Cys Glu Gly Tyr Phe Gly Asn Gly Phe Thr Leu
65                  70                  75                  80

Lys Val Asp Leu Leu Lys Thr Ser Pro Glu Phe His Arg Lys Phe Gly
                85                  90                  95

Asp Asn Thr Val Ser Gly Asp Gly Gly Trp Phe Arg Cys Phe Phe Ser
            100                 105                 110

Glu Thr Leu Gln Ser Ser Ile Cys Glu Gly Gly Ala Ile Arg Met Asn
        115                 120                 125

Pro Asp Asp Ile Leu Met Ser Arg Gly Gly Lys Leu Glu Ser Val
    130                 135                 140

Ile Gly Arg Asn Glu Asp Asp Glu Leu Pro Met Phe Lys Asn Gly Ala
145                 150                 155                 160

Phe Gln Ile Glu Val Thr Asp Lys Leu Lys Ile Gly Lys Lys Leu Val
                165                 170                 175

Asp Lys Lys Phe Leu Asn Lys Tyr Leu Pro Gly Gly Ala Ile Ser Arg
            180                 185                 190

His Thr Met Arg Glu Leu Ile Asp Ser Ile Gln Leu Val Gly Ala Asp
        195                 200                 205

Glu Phe His Cys Ser Glu Trp Val Glu Glu Pro Ser Leu Leu Ile Thr
    210                 215                 220

Arg Phe Glu Tyr Ala Asn Leu Phe His Thr Val Thr Asp Trp Tyr Ser
225                 230                 235                 240

Ala Tyr Ala Ala Ser Arg Val Thr Gly Leu Pro Ser Arg Pro Asn Leu
                245                 250                 255

Val Phe Val Asp Gly His Cys Glu Thr Gln Leu Glu Glu Thr Trp Lys
            260                 265                 270

Ala Leu Phe Ser Ser Leu Thr Tyr Ala Lys Asn Phe Ser Gly Pro Val
        275                 280                 285

Cys Phe Arg His Ala Val Leu Ser Pro Leu Gly Tyr Glu Thr Ala Leu
    290                 295                 300

Phe Lys Gly Leu Ser Glu Thr Ile Asp Cys Asn Gly Ala Ser Ala His
305                 310                 315                 320

Asp Leu Trp Gln Lys Pro Asp Asp Lys Lys Thr Ala Arg Leu Ser Glu
                325                 330                 335
```

-continued

```
Phe Gly Glu Met Ile Arg Ala Ala Phe Gly Phe Pro Val Asp Arg Gln
            340                 345                 350

Asn Ile Pro Arg Thr Val Thr Gly Pro Asn Val Leu Phe Val Arg Arg
        355                 360                 365

Glu Asp Tyr Leu Ala His Pro Arg His Gly Gly Lys Val Gln Ser Arg
    370                 375                 380

Leu Ser Asn Glu Glu Leu Val Phe Asp Ser Ile Lys Ser Trp Ala Leu
385                 390                 395                 400

Asn His Ser Glu Cys Lys Leu Asn Val Ile Asn Gly Leu Phe Ala His
                405                 410                 415

Met Ser Met Lys Glu Gln Val Arg Ala Ile Gln Asp Ala Ser Val Ile
            420                 425                 430

Val Gly Ala His Gly Ala Gly Leu Thr His Ile Val Ser Ala Ala Pro
        435                 440                 445

Lys Ala Val Ile Leu Glu Ile Ile Ser Ser Glu Tyr Arg Arg Pro His
    450                 455                 460

Phe Ala Leu Ile Ala Gln Trp Lys Gly Leu Glu Tyr His Pro Ile Tyr
465                 470                 475                 480

Leu Glu Gly Ser Tyr Ala Asp Pro Pro Val
                485                 490
```